US010011610B2

(12) United States Patent
Remick et al.

(10) Patent No.: US 10,011,610 B2
(45) Date of Patent: Jul. 3, 2018

(54) SELECTIVE BACE1 INHIBITORS

(71) Applicant: Eli Lilly and Company, Indianapolis, IN (US)

(72) Inventors: David Michael Remick, Fishers, IN (US); Simon James Richards, Surrey (GB); Adam Jan Sanderson, Surrey (GB)

(73) Assignee: Eli Lilly and Company, Indianapolis, IN (US)

( * ) Notice: Subject to any disclaimer, the term of this patent is extended or adjusted under 35 U.S.C. 154(b) by 153 days.

(21) Appl. No.: 15/135,580

(22) Filed: Apr. 22, 2016

(65) Prior Publication Data
US 2016/0318953 A1 Nov. 3, 2016

Related U.S. Application Data

(60) Provisional application No. 62/154,242, filed on Apr. 29, 2015.

(51) Int. Cl.
*C07D 513/04* (2006.01)
*C07C 309/04* (2006.01)
*C07C 309/31* (2006.01)

(52) U.S. Cl.
CPC .......... *C07D 513/04* (2013.01); *C07C 309/04* (2013.01); *C07C 309/31* (2013.01)

(58) Field of Classification Search
CPC .... C07D 513/04; C07C 309/31; C07C 309/04
See application file for complete search history.

(56) References Cited

U.S. PATENT DOCUMENTS

| 7,868,000 | B2 | 1/2011 | Zhu |
| 8,158,620 | B2 | 4/2012 | Suzuki |
| 8,198,269 | B2 | 6/2012 | Motoki |
| 8,278,441 | B2 | 10/2012 | Mergott |
| 8,338,407 | B2 | 12/2012 | Hall |
| 8,592,408 | B2 | 11/2013 | Hall et al. |
| 8,598,161 | B2 | 12/2013 | Wu |
| 8,637,504 | B2 | 1/2014 | Hori |
| 8,822,455 | B2 | 9/2014 | Dimopoulos |
| 8,841,293 | B1 | 9/2014 | Green et al. |
| 9,175,013 | B2 | 11/2015 | Takaishi |
| 9,522,923 | B2 | 12/2016 | Richards et al. |

FOREIGN PATENT DOCUMENTS

| EP | 2233474 B1 | 8/2015 |
| JP | 2014/101354 A | 6/2014 |
| WO | WO2011071057 | 6/2011 |
| WO | WO2012098461 | 7/2012 |
| WO | WO2014015125 | 1/2014 |
| WO | 2017/200863 A1 | 11/2017 |
| WO | 2018/031334 A1 | 2/2018 |

OTHER PUBLICATIONS

Oehlrich, D., Bioorg. Med. Chem. Lett. 24, pp. 2033-2045 (2014).
U.S. Appl. No. 15/045,305.
Written Opinion of International Searching Authority PCT/US2016/028896.
International Search Report and Written Opinion of the International Searching Authority.
Japan Patent Office Search Report dated May 9, 2017 for Japan Patent Application No. 2016-567244 (Japanese with English Translation).
Anderson and Flora, Chapter 34, Practice of Medicinal Chemistry 1996 (Japanese and English equivalent).
Noriyuki Takada, Pharmstage vol. 6(10) pp. 20-25 (2007) (Japanese with English Translation).
Noriaki Hirayama, Organic Compound Crystal Manufacturing Handbook—Principles and Knowhow, pp. 57-84 (Jul. 25, 2008) (Japanese with English Translation).

*Primary Examiner* — Sreeni Padmanabhan
*Assistant Examiner* — Jody Karol
(74) *Attorney, Agent, or Firm* — Nelsen L. Lentz

(57) ABSTRACT

The present invention provides a compound of Formula I:

Formula I or a pharmaceutically acceptable salt thereof.

20 Claims, No Drawings

SELECTIVE BACE1 INHIBITORS

The present invention relates to novel selective BACE1 inhibitors, to pharmaceutical compositions comprising the compounds, to methods of using the compounds to treat physiological disorders, and to intermediates and processes useful in the synthesis of the compounds.

The present invention is in the field of treatment of Alzheimer's disease and other diseases and disorders involving amyloid β (Abeta) peptide, a neurotoxic and highly aggregatory peptide segment of the amyloid precursor protein (APP). Alzheimer's disease is a devastating neurodegenerative disorder that affects millions of patients worldwide. In view of the currently approved agents on the market which afford only transient, symptomatic benefits to the patient rather than halting, slowing, or reversing the disease, there is a significant unmet need in the treatment of Alzheimer's disease.

Alzheimer's disease is characterized by the generation, aggregation, and deposition of Abeta in the brain. Complete or partial inhibition of β-secretase (β-site amyloid precursor protein-cleaving enzyme; BACE) has been shown to have a significant effect on plaque-related and plaque-dependent pathologies in mouse models suggesting that even small reductions in Abeta peptide levels might result in a long-term significant reduction in plaque burden and synaptic deficits, thus providing significant therapeutic benefits, particularly in the treatment of Alzheimer's disease. In addition, two homologs of BACE have been identified which are referred to as BACE1 and BACE2, and it is believed that BACE1 is the most clinically important to development of Alzheimer's disease. BACE1 is mainly expressed in the neurons while BACE2 has been shown to be expressed primarily in the periphery (See D. Oehlrich, *Bioorg. Med. Chem. Lett.*, 24, 2033-2045 (2014)). In addition, BACE2 may be important to pigmentation as it has been identified as playing a role in the processing of pigment cell-specific melanocyte protein (See L. Rochin, et al., *Proc. Natl. Acad. Sci. USA*, 110(26), 10658-10663 (2013)). BACE inhibitors with central nervous system (CNS) penetration, particularly inhibitors that are selective for BACE1 over BACE2 are desired to provide treatments for Abeta peptide-mediated disorders, such as Alzheimer's disease.

U.S. Pat. No. 8,158,620 discloses fused aminodihydrothiazine derivatives which possess BACE1 inhibitory activity and are further disclosed as useful therapeutic agents for a neurodegenerative disease caused by Abeta peptide, such as Alzheimer's type dementia. In addition, U.S. Pat. No. 8,338,407 discloses certain fused aminodihydrothiazine derivatives having BACE1 inhibitory effect useful in treating certain neurodegenerative diseases, such as Alzheimer-type dementia.

The present invention provides certain novel compounds that are inhibitors of BACE. In addition, the present invention provides certain novel compounds that are selective inhibitors of BACE1 over BACE2. Furthermore, the present invention provides certain novel compounds which penetrate the CNS. The present invention also provides certain novel compounds which have the potential for an improved side-effect profile, for example, through selective inhibition of BACE1 over BACE2.

Accordingly, the present invention provides a compound of Formula I:

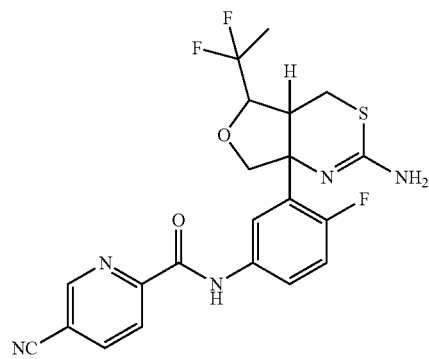

Formula I or a pharmaceutically acceptable salt thereof.

In addition, the present invention provides a compound of Formula Ia:

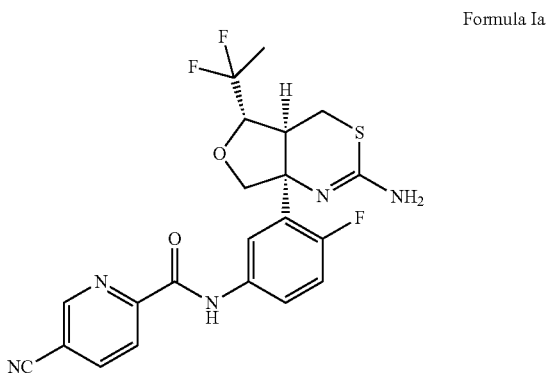 [SMILES: CC(F)(F)[C@H]1OC[C@]2(c3cc(NC(=O)c4ccc(C#N)cn4)ccc3F)N=C(N)SC[C@H]12]

Formula Ia or a pharmaceutically acceptable salt thereof.

The present invention also provides a method of treating Alzheimer's disease in a patient, comprising administering to a patient in need of such treatment an effective amount of a compound of Formulas I or Ia, or a pharmaceutically acceptable salt thereof.

The present invention further provides a method of treating the progression of mild cognitive impairment to Alzheimer's disease in a patient, comprising administering to a patient in need of such treatment an effective amount of a compound of Formulas I or Ia, or a pharmaceutically acceptable salt thereof. The present invention also provides a method of inhibiting BACE in a patient, comprising administering to a patient in need of such treatment an effective amount of a compound of Formulas I or Ia, or a pharmaceutically acceptable salt thereof. The present invention also provides a method for inhibiting BACE-mediated cleavage of amyloid precursor protein, comprising administering to a patient in need of such treatment an effective amount of a compound of Formulas I or Ia, or a pharmaceutically acceptable salt thereof. The invention further provides a method for inhibiting production of Abeta peptide, comprising administering to a patient in need of such treatment an effective amount of a compound of Formulas I or Ia, or a pharmaceutically acceptable salt thereof.

Furthermore, this invention provides a compound of Formulas I or Ia, or a pharmaceutically acceptable salt thereof for use in therapy, in particular for the treatment of Alzheimer's disease or for preventing the progression of mild cognitive impairment to Alzheimer's disease. Even furthermore, this invention provides the use of a compound of Formulas I or Ia, or a pharmaceutically acceptable salt thereof, for the manufacture of a medicament for the treatment of Alzheimer's disease.

The invention further provides a pharmaceutical composition, comprising a compound of Formulas I or Ia, or a pharmaceutically acceptable salt thereof, with one or more pharmaceutically acceptable carriers, diluents, or excipients. The invention further provides a process for preparing a pharmaceutical composition, comprising admixing a compound of Formulas I or Ia, or a pharmaceutically acceptable salt thereof, with one or more pharmaceutically acceptable carriers, diluents, or excipients. This invention also encompasses novel intermediates and processes for the synthesis of the compounds of Formulas I and Ia.

Mild cognitive impairment has been defined as a potential prodromal phase of dementia associated with Alzheimer's disease based on clinical presentation and on progression of patients exhibiting mild cognitive impairment to Alzheimer's dementia over time. (Morris, et al., *Arch. Neurol.*, 58, 397-405 (2001); Petersen, et al., *Arch. Neurol.*, 56, 303-308 (1999)). The term "preventing the progression of mild cognitive impairment to Alzheimer's disease" includes restraining, slowing, stopping, or reversing the progression of mild cognitive impairment to Alzheimer's disease in a patient.

As used herein, the terms "treating" or "to treat" includes restraining, slowing, stopping, or reversing the progression or severity of an existing symptom or disorder.

As used herein, the term "patient" refers to a human.

The term "inhibition of production of Abeta peptide" is taken to mean decreasing of in vivo levels of Abeta peptide in a patient.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of the present invention are generally effective over a wide dosage range. For example, dosages per day normally fall within the range of about 0.01 to about 20 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the present invention are preferably formulated as pharmaceutical compositions administered by any route which makes the compound bioavailable, including oral and transdermal routes. Most preferably, such compositions are for oral administration. Such pharmaceutical compositions and processes for preparing same are well known in the art. (See, e.g., Remington: The Science and Practice of Pharmacy, L. V. Allen, Editor, 22$^{nd}$ Edition, Pharmaceutical Press, 2012).

The compounds of Formulas I and Ia, or pharmaceutically acceptable salts thereof are particularly useful in the treatment methods of the invention, but certain groups, substituents, and configurations are preferred. The following paragraphs describe such preferred groups, substituents, and configurations. It will be understood that these preferences are applicable both to the treatment methods and to the new compounds of the invention.

Thus, the compound of Formula I wherein the fused bicyclic ring is in the cis configuration, or pharmaceutically acceptable salt thereof, is preferred. For example, one of ordinary skill in the art will appreciate that the compound of Formula Ia is in the cis relative configuration for the centers labeled 4a and 7a as shown in Scheme A below. In addition, the preferred relative configuration for the three chiral centers of Formula Ia is shown in Scheme A wherein the difluoroethyl substituent at position 5 is in the cis configuration relative to the hydrogen at position 4a and the substituted phenyl substituent at position 7a:

Scheme A

Formula Ia

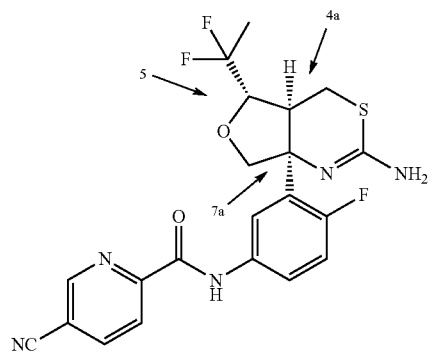

Further compounds of the present invention include:

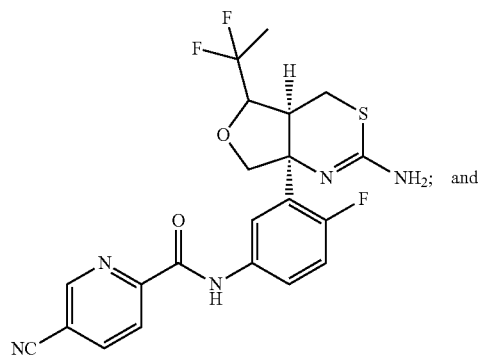

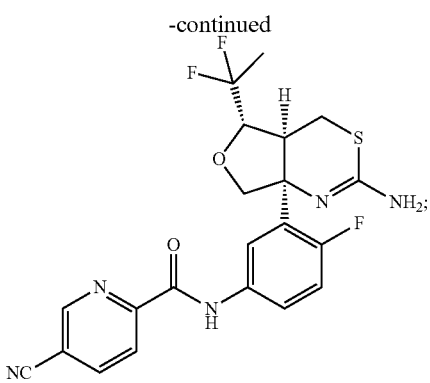

and pharmaceutically acceptable salts thereof.

Although the present invention contemplates all individual enantiomers and diastereomers, as well as mixtures of the enantiomers of said compounds, including racemates, the compounds with the absolute configuration as set forth below are particularly preferred:

N-[3-[(4aS,5S,7aS)-2-amino-5-(1,1-difluoroethyl)-4,4a,5,7-tetrahydrofuro[3,4-d][1,3]thiazin-7a-yl]-4-fluoro-phenyl]-5-cyano-pyridine-2-carboxamide, and the pharmaceutically acceptable salts thereof.

In addition, N-[3-[(4aS,5S,7aS)-2-amino-5-(1,1-difluoroethyl)-4,4a,5,7-tetrahydrofuro[3,4-d][1,3]thiazin-7a-yl]-4-fluoro-phenyl]-5-cyano-pyridine-2-carboxamide;

N-[3-[(4aS,5S,7aS)-2-amino-5-(1,1-difluoroethyl)-4,4a,5,7-tetrahydrofuro[3,4-d][1,3]thiazin-7a-yl]-4-fluoro-phenyl]-5-cyano-pyridine-2-carboxamide methanenesulfonate;

N-[3-[(4aS,5S,7aS)-2-amino-5-(1,1-difluoroethyl)-4,4a,5,7-tetrahydrofuro[3,4-d][1,3]thiazin-7a-yl]-4-fluoro-phenyl]-5-cyano-pyridine-2-carboxamide 4-methylbenzenesulfonate; and N-[3-[(4aS,5S,7aS)-2-amino-5-(1,1-difluoroethyl)-4,4a,5,7-tetrahydrofuro[3,4-d][1,3]thiazin-7a-yl]-4-fluoro-phenyl]-5-cyano-pyridine-2-carboxamide 4-methylbenzenesulfonate hemihydrate, are especially preferred.

N-[3-[(4aS,5S,7aS)-2-amino-5-(1,1-difluoroethyl)-4,4a,5,7-tetrahydrofuro[3,4-d][1,3]thiazin-7a-yl]-4-fluoro-phenyl]-5-cyano-pyridine-2-carboxamide 4-methylbenzenesulfonate; and N-[3-[(4aS,5S,7aS)-2-amino-5-(1,1-difluoroethyl)-4,4a,5,7-tetrahydrofuro[3,4-d][1,3]thiazin-7a-yl]-4-fluoro-phenyl]-5-cyano-pyridine-2-carboxamide 4-methylbenzenesulfonate hemihydrate are most especially preferred.

One of ordinary skill in the art will appreciate that compounds of the invention can exist in tautomeric forms, as depicted below in Scheme B. When any reference in this application to one of the specific tautomers of the compounds of the invention is given, it is understood to encompass both tautomeric forms and all mixtures thereof.

Additionally, certain intermediates described in the following preparations may contain one or more nitrogen protecting groups. It is understood that protecting groups may be varied as appreciated by one of skill in the art depending on the particular reaction conditions and the particular transformations to be performed. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

Individual isomers, enantiomers, and diastereomers may be separated or resolved by one of ordinary skill in the art at any convenient point in the synthesis of compounds of the invention, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994).

A pharmaceutically acceptable salt of the compounds of the invention, such as a hydrochloride salt, can be formed, for example, by reaction of an appropriate free base of a compound of the invention, an appropriate pharmaceutically acceptable acid such as hydrochloric acid in a suitable solvent such as diethyl ether under standard conditions well known in the art. Additionally, the formation of such salts can occur simultaneously upon deprotection of a nitrogen protecting group. The formation of such salts is well known and appreciated in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

Certain abbreviations are defined as follows: "APP" refers to ameloid precursor protein; "BSA" refers to Bovine Serum Albumin; "CDI" refers to 1,1'-carbonyldiimidazole; "cDNA" refers to complementary deoxyribonucleic acid; "DAST" refers to diethylaminosulfur trifluoride; "DCC" refers to 1,3-dicyclohexylcarbodiimide; "DIC" refers to 1,3-diisopropylcarbodiimide; "DIPEA" refers to N,N-diisopropylethylamine; "DMAP" refers to 4-dimethylaminopyridine; "DMSO" refers to dimethyl sulfoxide; "EBSS" refers to Earle's Balances Salt Solution; "EDCI" refers to 1-(3-dimethylaminopropyl)-3-ethylcarbodiimide hydrochloride; "ELISA" refers to enzyme-linked immunosorbent assay; "F12" refers to Ham's F12 medium; "FBS" refers to Fetal Bovine Serum; "Fc" refers to fragment crystallizable;

Scheme B

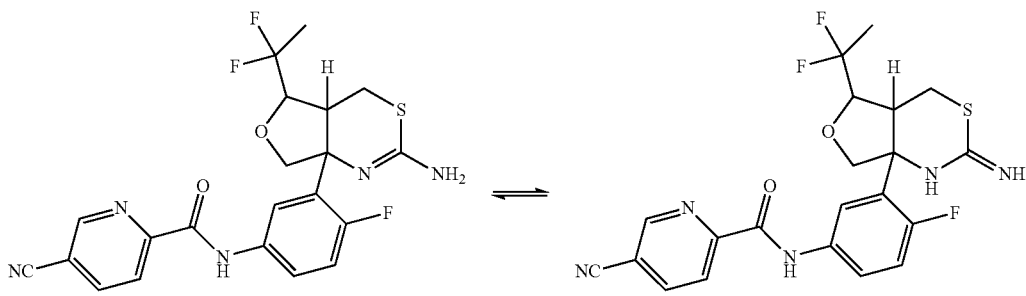

"FLUOLEAD™" refers to 4-tert-butyl-2,6-dimethylphenyl-sulfur trifluoride; "FRET" refers to fluorescence resonance energy transfer; "HATU" refers to (dimethylamino)-N,N-dimethyl(3H-[1,2,3]triazolo[4,5-b]pyridin-3-yloxy)methaniminium hexafluorophosphate; "HBTU" refers to (1H-benzotriazol-1-yloxy)(dimethylamino)-N,N-dimethylmethaniminium hexafluorophosphate; "HEK" refers to human embryonic kidney; "HF-pyridine" refers to hydrogen fluoride pyridine or Olah's reagent or poly(pyridine fluoride); "HOBT" refers to 1-hydroxylbenzotriazole hydrate; "IC$_{50}$" refers to the concentration of an agent that produces 50% of the maximal inhibitory response possible for that agent; "HRP" refers to horseradish peroxidase; "IgG$_1$" refers to immunoglobulin-like domain Fc-gamma receptor; "MBP" refers to maltose binding protein; "MEM" refers to Minimum Essential Medium; "PBS" refers to phosphate buffered saline; "PDAPP" refers to platelet derived amyloid precursor protein; "PyBOP" refers to (benzotriazol-1-yl-oxytripyrrolidinophosphonium hexafluorophosphate); "PyBrOP" refers to bromo(tri-pyrrolidinyl)phosphoniumhexafluorophosphate; "RFU" refers to relative fluorescence unit; "RT-PCR" refers to reverse transcription polymerase chain reaction; "SDS-PAGE" refers to sodium dodecyl sulfate polyacrylamide gel electrophoresis; "THF" refers to tetrahydrofuran; "TMB" refers to tetramethylbenzidine; "TMEM" refers to transmembrane protein; "Tris" refers to tris(hydroxymethyl)aminomethane; "trityl" refers to a group of the formula "(Ph)$_3$C—"; "XRD" refers to X-Ray Powder Diffraction; "XtalFluor-E® or DAST difluorosulfinium salt" refers to (diethylamino)difluorosulfonium tetrafluoroborate or N,N-diethyl-S,S-difluorosulfiliminium tetrafluoroborate; and "XtalFluor-M® or morpho-DAST difluorosulfinium salt" refers to difluoro(morpholino)sulfonium tetrafluoroborate or difluoro-4-morpholinylsulfonium tetrafluoroborate.

It is understood by one of ordinary skill in the art that the terms "tosylate", "toluenesulfonic acid", "p-toluenesulfonic acid", and "4-methylbenzene sulfonic acid" refer to the compound of the following structure:

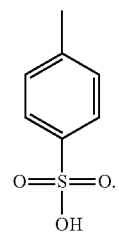

The compounds of the present invention, or salts thereof, may be prepared by a variety of procedures known to one of ordinary skill in the art, some of which are illustrated in the schemes, preparations, and examples below. One of ordinary skill in the art recognizes that the specific synthetic steps for each of the routes described may be combined in different ways, or in conjunction with steps from different schemes, to prepare compounds of the invention, or salts thereof. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. Without limiting the scope of the invention, the following schemes, preparations, and examples are provided to further illustrate the invention.

Scheme 1

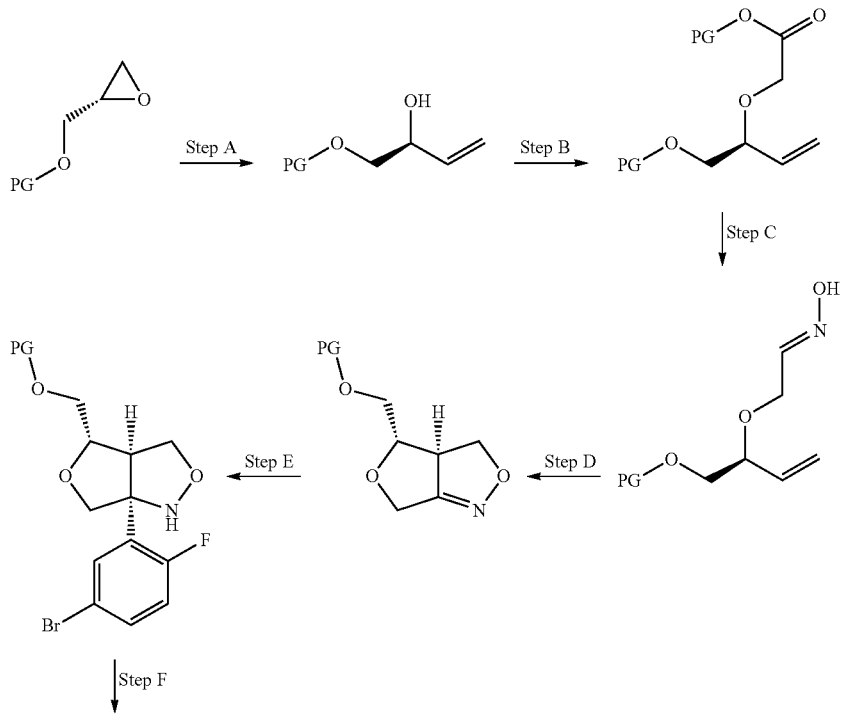

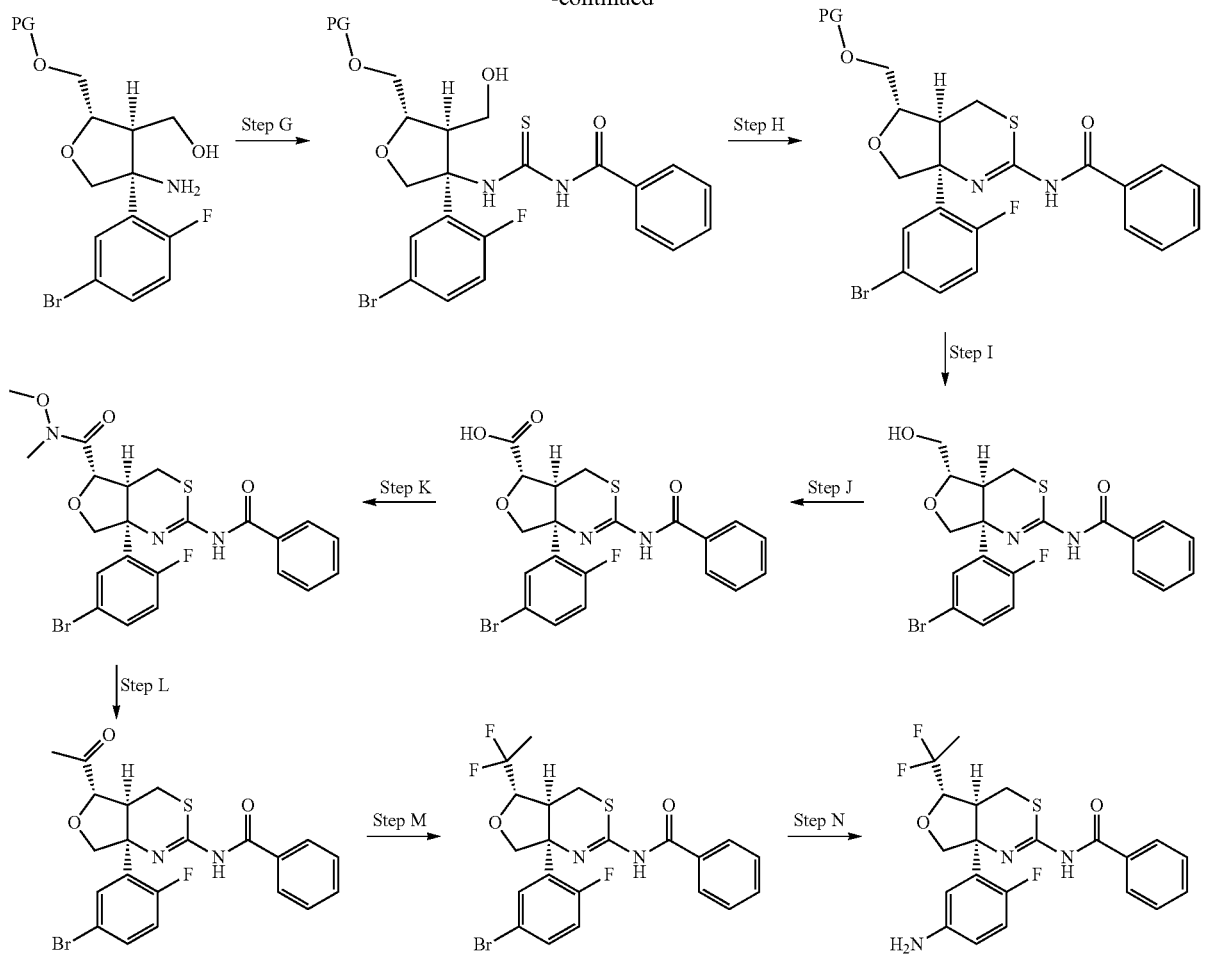

In Scheme 1, step A, trimethylsulfonium iodide is treated with an organic base such as n-butyllithium at a temperature of about −50° C. in a solvent such as THF. A protected oxymethyl oxirane, protected with a suitable protecting group, such as a trityl group, is then added to the basic solution at −10° C. and allowed to stir for about 2 hours to give the protected product of Scheme 1, Step A. "PG" is a protecting group developed for the amino group or oxygen group such as carbamates, amides, or ethers. Such protecting groups are well known and appreciated in the art. The protected product of Step A is reacted with an α-haloester such as tert-butoxy bromoacetate using tetra-N-butylammonium sulfate or other quaternary ammonium salt phase transfer catalysts in a solvent such as toluene and an aqueous inorganic base such as sodium hydroxide at about room temperature to give the compound of Scheme 1, Step B. Such alkylations are well known in the art. Alternatively a base such as 60% sodium hydride in oil with solvents such as N,N-dimethylformamide or THF and a temperature range of 0 to 100° C. can be used to give the protected product of Step B. The tert-butoxy carbonyl acetate is converted to an oxime over a 2-step procedure. A reducing agent such as isobutylaluminum hydride in hexanes is added dropwise at a temperature of about −70° C. followed by the dropwise addition of an aqueous acid such as hydrochloric acid at a temperature of about −60° C. The work-up is accomplished with an organic extraction to give the intermediate material. This material is dissolved in an organic solvent such as dichloromethane and treated with sodium acetate followed by hydroxylamine hydrochloride to give the oxime product of Step C. The oxime product of Scheme 1, Step C can be converted to the bicyclic 4,5-dihydroisoxazole product of Step D in a 3+2 cyclization by several methods such as using an aqueous solution of sodium hypochlorite or an alternative oxidant such as N-chlorosuccinimide and in a solvent such as tert-butyl methyl ether, toluene, dichloromethane, or xylene at a temperature of about 10-15° C. or with heating. The 2-fluoro, 5-bromo phenyl group can be added to the dihydroisoxazole by generating the organometallic reagent. The organometallic reagent can be generated from 4-bromo-1-fluoro-2-iodo-benzene using halogen-metal exchange with reagents such as n-butyllithium or isopropylmagnesium chloride lithium chloride complex and dropwise addition at a temperature range of about −78° C. to 15° C. in a solvent such as THF. A Lewis acid such as boron trifluoride diethyl etherate is then added to give the product of Scheme 1, Step E. The resulting bicyclic tetrahydroisoxazole can be treated with zinc in acetic acid to form the ring opened product of Scheme 1, Step F. An alternate method to open the isoxazole ring uses Raney Nickel in a polar solvent such as ethanol under pressure with hydrogenation conditions. The product of Step F can then be reacted with benzoyl isothiocyanate in a solvent such as dichloromethane or THF at a temperature of about 5° C. to room temperature to give the thiourea compound of Step G. The thiazine ring can be formed using trifluoromethanesulfonic anhydride and an organic base such as pyridine in a solvent such as dichloromethane at a temperature of about −20° C. to give the product of Step H. The hydroxymethyl protecting group such as a trityl group can be removed in Scheme 1, Step I using methods well known in the art such as formic acid at room temperature to give the compound of Step I. The hydroxy methyl can be oxidized to the carboxylic acid using oxidizing agents such as 2-iodoxybenzoic acid (IBX) at room temperature in a solvent such as DMSO or portionwise addition of (diacetoxyiodo)benzene in a solvent such as acetonitrile with stirring at a temperature of about 5° C. to give the compound of Scheme 1, Step J. The Weinreb amide is prepared in Scheme 1, Step K from the acid product of Step J with the addition of N,O-dimethylhydroxylamine hydrochloride, an organic base, such as triethylamine, and a coupling reagent such as HATU. The mixture is stirred at room temperature to give the product of Step K. Other coupling agents that could be used include CDI, carbodiimides such as DCC, DIC, or EDCI or other uronium or phosphonium salts of non-nucleophilic anions, such as HBTU, PyBOP, and PyBrOP. The Weinreb amide is then converted to the ketone using an organometallic reagent such as a Grignard reagent or an organolithium reagent in Step L in a solvent such as THF. Specifically, methylmagnesium bromide as a solution in solvents such as ether or 2-methyltetrahydrofuran can be added to the Weinreb amide at a temperature of about −78° C. to −40° C. to give the ketone of Step L. In Scheme 1, Step M, the methyl ketone group of the compound of Step L is converted to a difluoroethyl group using difluoro(morpholino)sulfonium tetrafluoroborate in a solvent such as dichloromethane at about 0° C. followed by the dropwise addition of triethylamine trihydrofluoride and stirring at 0° C. to room temperature to give the compound of Scheme 1, Step M. Alternatively, other fluorinating agents that may be used which are well known in the art are Deoxo-Fluor®, DAST, XtalFluor-E® or XtalFluor-M® with an additive such as triethylamine tri(hydrogen fluoride) or FLUO-LEAD™ using an additive such as HF-pyridine. The 5-bromo of the phenyl is converted to the amine using (1R,2R)—N,N'-dimethyl-1,2-cyclohexanediamine in a solvent such as ethanol and adding sodium azide followed by sodium ascorbate and cupric sulfate. The reaction is heated to about 80° C. for several hours and then worked up with an extraction using a solvent such as ethyl acetate. The intermediate is then reduced under hydrogenation conditions using palladium on carbon such as 10% palladium in solvents such as ethanol and THF at a pressure of about 50 psi of hydrogen to give the aniline product of Scheme 1, Step N.

Scheme 1a

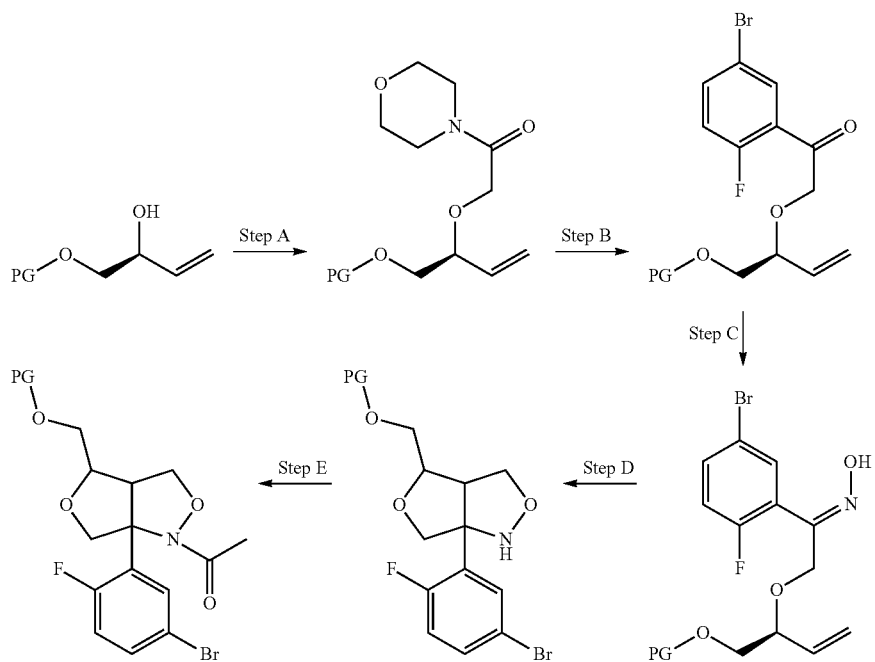

Alternatively in Scheme 1a, the protected product of Scheme 1, Step A, can be treated with 4-(2-chloroacetyl)morpholino and a base such as tetrabutyl ammonium hydrogen sulfate in a solvent such as toluene at a temperature of about 5° C. to give the product of Scheme 1a, Step A. The morpholino group can then serve as a leaving group in Scheme 1a, Step B. For example, the product of Scheme 1a, Step A can be treated with the appropriate Grignard reagent which can be prepared in situ from isopropyl magnesium chloride lithium chloride complex and 4-bromo-1-fluoro-2-iodobenzene or if the appropriate Grignard reagent is available, the reagent can be added directly to the product of Scheme 1a, Step A at a temperature of about 5° C. to give the product of Scheme 1a, Step B. The carbonyl acetate can be converted to an oxime with hydroxylamine hydrochloride and sodium acetate with heating to about 50° C. to give the product of Scheme 1a, Step C. The oxime product of Scheme 1a, Step C can then be converted to the product of Scheme 1a, Step D (the same product as Scheme 1, Step E) using hydroquinone in a solvent such as toluene and heating to reflux. The amine product of Scheme 1a, Step D can be acylated with acetyl chloride using an organic base such as DMAP and pyridine in a solvent such as dichloromethane at a temperature of about 0-5° C. to give the product of Scheme 1a, Step E. The product of Scheme 1a, Step E can then be converted to the product of Scheme 2, Step A as discussed below.

Step A. The hydroxy methyl product of Scheme 2, Step A can be oxidized to the carboxylic acid product of Scheme 2, Step B in a manner analogous to the procedure described in Scheme 1, Step J, and the Weinreb amide can be further prepared in a manner analogous to the procedure described Scheme 2

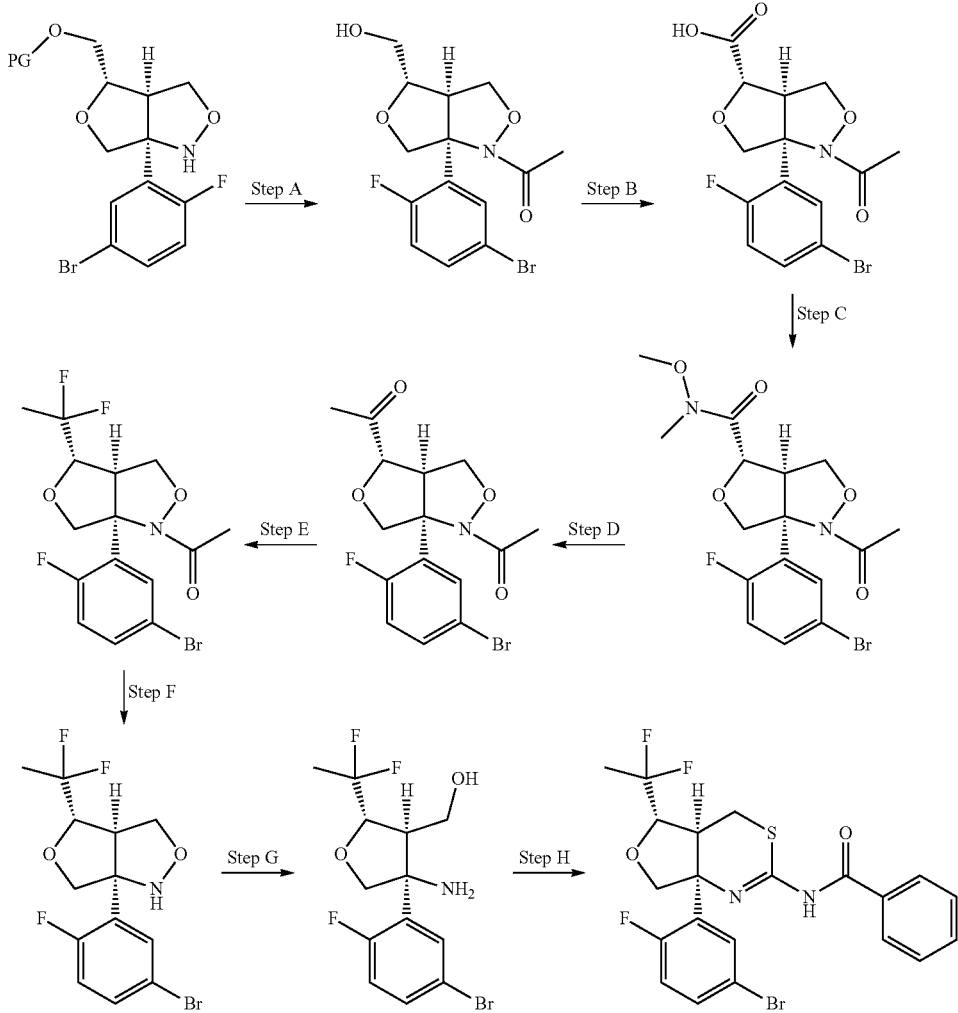

In an alternate route, as described in Scheme 2, the isoxazole nitrogen of the compound of Scheme 1, Step E, is protected with an acetyl group and the protecting group of the hydroxy methyl is removed in a two-step procedure. For example, the tetrahydroisoxazole is treated with an organic base such as DMAP and pyridine in a solvent such as dichloromethane and acetyl chloride is added. The temperature is maintained below about 10° C. and then allowed to stir at about room temperature. The reaction is diluted with water and extracted with a solvent such as dichloromethane. The organic extracts are washed with an aqueous acid such as 1 N hydrochloric acid and the aqueous extracted again with a solvent such as dichloromethane followed by an aqueous wash. The organic solvent is partially removed and an acid such as formic acid is added to deprotect the hydroxy methyl. The mixture can be stirred at room temperature or heated to a temperature of about 40° C. until deprotection of the hydroxy is complete to give the compound of Scheme 2, Step A. The hydroxy methyl product of Scheme 2, Step A can be oxidized to the carboxylic acid product of Scheme 2, Step B in a manner analogous to the procedure described in Scheme 1, Step J, and the Weinreb amide can be further prepared in a manner analogous to the procedure described in Scheme 1, Step K using a coupling agent such as CDI in a portionwise addition with a solvent such as dichloromethane, cooling to −20° C. and stirring for about 1 hour and adding N,O-dimethylhydroxylamine hydrochloride portionwise. Further additions of CDI and N,O-dimethylhydroxylamine can be added until complete reaction is observed to give the Weinreb amide product of Scheme 2, Step C. The ketone of Scheme 2, Step D can be formed from the Weinreb amide in a manner analogous to the procedure described in Scheme 1, Step L. The ketone of Step D can be converted to a difluoroethyl group in a manner analogous to the procedure described in Scheme 1, Step M to give the product of Scheme 2, Step E. The acetyl tetrahydroisoxazole can deprotected under acidic conditions well known in the art such as using hydrochloric acid and heating to about 100° C. to give the product of Scheme 2, Step F. The bicyclic tetrahydroisoxazole can be treated with zinc in acetic acid to form the ring opened product of Scheme 2, Step G in a manner analogous to the procedure described in Scheme 1, Step F. The thiazine product of Scheme 2, Step H can be prepared in a one pot 2 step reaction using benzoyl isothiocyanate in a manner analogous to the procedure described in Scheme 1, Step G and H. The mixture is evaporated to a residue and cyclohexane is added. The mixture is heated to about 60° C. and methyl tert-butyl ether is added to dissolve the residue. The solution is filtered and concentrated to dryness. The thiazine ring can then be formed in a manner analogous to the procedure described in Scheme 1, Step H to give the product of Scheme 2, Step H.

phosphonic anhydride (T3P®) can be used in place of the more traditional coupling reagents. Additives such as DMAP may be used to enhance the reaction. Alternatively, the aniline amine can be acylated using substituted benzoyl chlorides in the presence of a base such as triethylamine or pyridine. In Scheme 3, Step B, the protected thiazine amine can then be deprotected with an organic base such as pyridine and O-methylhydroxylamine hydrochloride in solvents such as THF and ethanol and an organic base such as pyridine to provide the compound of Formula Ia. Alternatively an inorganic base such as lithium hydroxide in methanol may be used to deprotect the thiazine to provide the compound of Formula Ia.

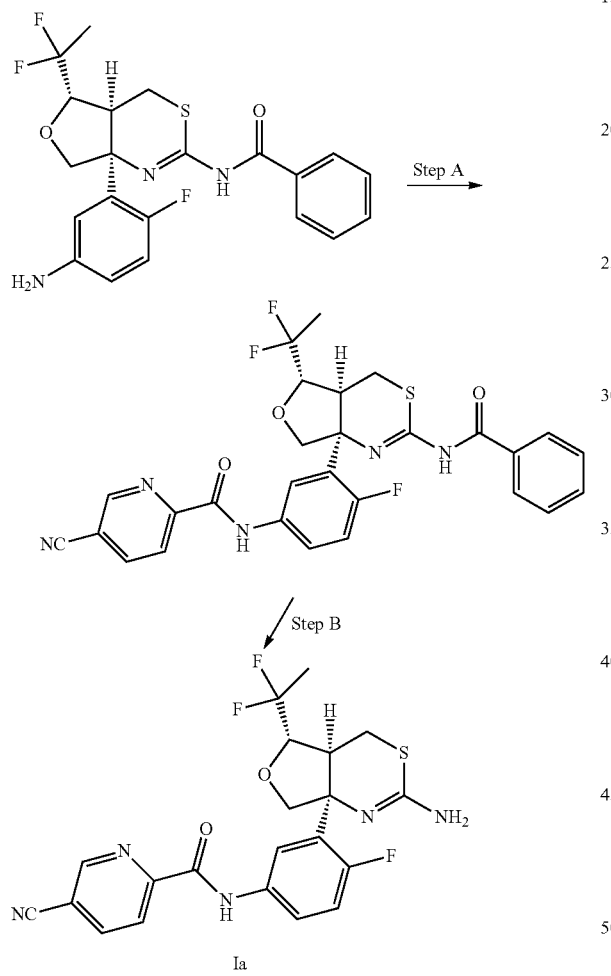

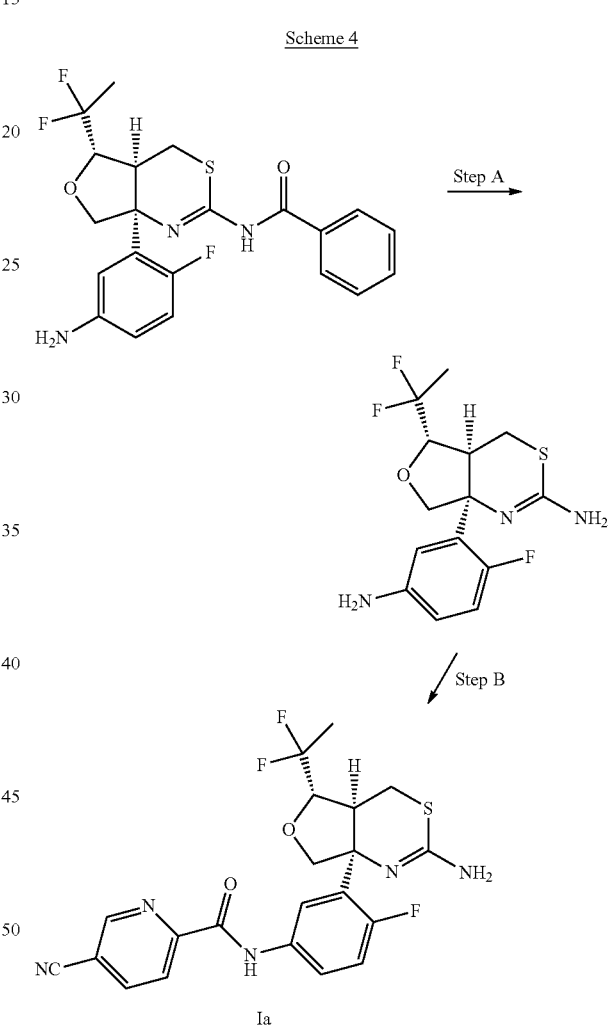

In Scheme 3, Step A, the aniline product of Scheme 1, Step N can be coupled with a heteroaromatic carboxylic acid utilizing coupling conditions well known in the art. One skilled in the art will recognize that there are a number of methods and reagents for amide formation resulting from the reaction of carboxylic acids and amines. For example, the reaction of an appropriate aniline with an appropriate acid in the presence of a coupling reagent and an amine base such as DIPEA or triethylamine, will give a compound of Scheme 3, Step A. Coupling reagents include carbodiimides such as DCC, DIC, EDCI, and aromatic oximes such as HOBt and HOAt. Additionally, uronium or phosphonium salts of non-nucleophilic anions such as HBTU, HATU, PyBOP, and PyBrOP or a cyclic phosphoric anhydride such as propyl- Alternatively, in Scheme 4, Step A, the aniline product of Scheme 1, Step N can be deprotected under standard conditions well known in the art, for example with an organic base such as pyridine and O-methylhydroxylamine hydrochloride in solvents such as THF and ethanol to provide the deprotected diamino compound. Alternatively an inorganic base such as lithium hydroxide in methanol may be used for the deprotection to provide the deprotected diamino compound.

In Scheme 4, Step B, the deprotected diamino compound can then be selectively coupled at the aniline amino group with a heteroaromatic carboxylic acid utilizing coupling conditions well known in the art to provide the compound of Formula Ia. One skilled in the art will recognize that there are a number of methods and reagents for amide formation resulting from the reaction of carboxylic acids and amines. For example, the reaction of an appropriate amine with an appropriate acid in the presence of a coupling reagent and an amine base such as DIPEA or triethylamine, will provide a compound of Formula Ia. Coupling reagents include carbodiimides such as DCC, DIC, EDCI, and aromatic oximes such as HOBt and HOAt. Additionally, uronium or phosphonium salts of non-nucleophilic anions such as HBTU, HATU, PyBOP, and PyBrOP or a cyclic phosphoric anhydride such as propylphosphonic anhydride (T3P®) can be used in place of the more traditional coupling reagents. Additives such as DMAP may be used to enhance the reaction.

aniline product of Scheme 5, Step A. The protected aniline and thiazine amine can then be deprotected stepwise. The trifluoroacetamide can be hydrolyzed using a base such as 7 N ammonia in methanol to give an aniline and protected thiazine, the same product of Scheme 1, Step N. The thiazine can then be deprotected under conditions well known in the art and described in Scheme 4, Step A using O-methylhydroxylamine hydrochloride in a solvent such as ethanol and THF with an organic base such as pyridine followed by heating to about 55° C. or stirring at room temperature followed by concentration and purification to give the product of Scheme 5, Step B. Alternatively, the order of deprotection could be reversed with the thiazine deprotected first and the aniline deprotected last.

The following preparations and examples further illustrate the invention.

Preparation 1

(2S)-1-Trityloxybut-3-en-2-ol

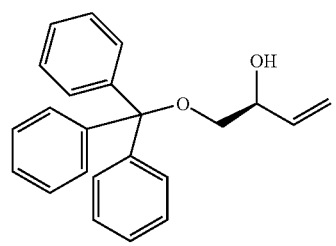 [SMILES: C=C[C@H](O)COC(c1ccccc1)(c1ccccc1)c1ccccc1]

Scheme 1, step A: Stir trimethylsulfonium iodide (193.5 g, 948.2 mmol) in THF (1264 mL) at ambient temperature for 75 minutes. Cool mixture to −50° C. and add n-butyllithium (2.5 mol/L in hexanes, 379 mL, 948.2 mmol) via cannula, over a period of 30 minutes. Allow the reaction to gradually warm to −30° C. and stir for 60 minutes. Add (2S)-2-trityloxymethyl oxirane (100 g, 316.1 mmol) portion wise, keeping the temperature below −10° C. After the complete addition, allow the reaction mixture to warm to room temperature and stir for 2 hours. Pour the reaction into saturated ammonium chloride, separate the phases, and extract the aqueous phase with ethyl acetate. Combine the organic layers and dry over magnesium sulfate. Filter and concentrate under reduced pressure to give a residue. Purify the residue by silica gel chromatography, eluting with methyl t-butyl ether:hexanes (10-15% gradient), to give the title compound (56.22 g, 54%). ES/MS m/z 353 (M+Na).

Alternate Preparation 1

(2S)-1-Trityloxybut-3-en-2-ol

Scheme 1a, step A starting material: Add triphenylmethyl chloride (287 g, 947.1 mmol), DMAP (7.71 g, 63.1 mmol) and triethylamine (140 g, 1383.5 mmol) to a solution of (2S)-but-2-ene-1,2-diol (prepared as in JACS, 1999, 121, 8649) (64.5 g, 631 mmol) in dichloromethane (850 mL). Stir for 24 hours at 24° C. Add 1 N aqueous citric acid (425 mL). Separate the layers and concentrate the organic extract under reduced pressure to dryness. Add methanol (900 mL) and cool to 5° C. for 1 hour. Collect the solids by filtration and wash with 5° C. methanol (50 mL). Discard the solids and concentrate the mother liquor under reduced pressure to

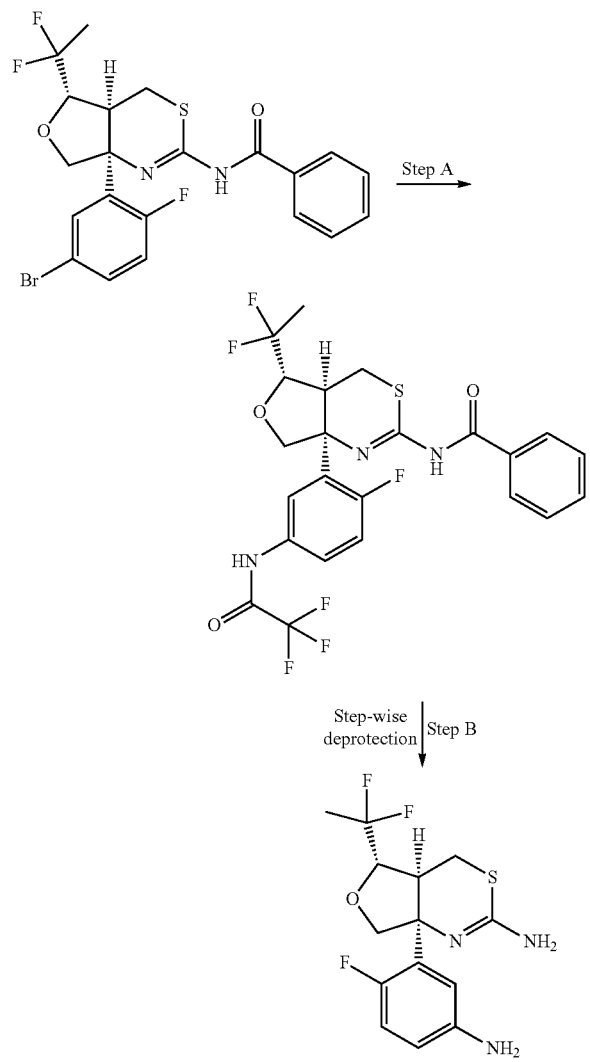

Scheme 5

Alternatively, in Scheme 5, the bromide product of Scheme 1, Step M is converted to a protected aniline using trifluoroacetamide, copper iodide, a diamine such as trans, racemic-N,N'-dimethyl-1,2-cyclohexane diamine, an inorganic base such as potassium carbonate, and sodium iodide with heating to about 100-130° C. to give the protected dryness. Add toluene (800 mL) and concentrate to a mass of 268 g to obtain the title compound (129 g, 67%) in a 48 wt % solution of toluene.

Preparation 2

1-Morpholino-2-[(1S)-1-(trityloxymethyl)allyloxy]ethanone

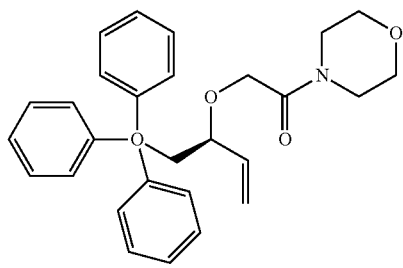

Scheme 1a, step A: Add tetrabutyl ammonium hydrogen sulfate (83.2 g, 245.0 mmol) and 4-(2-chloroacetyl)morpholine (638.50 g, 3902.7 mmol) to a solution of 1-trityloxybut-3-en-2-ol (832.4, 2519 mmol) in toluene (5800 mL) that is between 0 and 5° C. Add sodium hydroxide (1008.0 g, 25202 mmol) in water (1041 mL). Stir for 19 hours between 0 and 5° C. Add water (2500 mL) and toluene (2500 mL). Separate the layers and wash the organic extract with water (2×3500 mL). Concentrate the organic extract under reduced pressure to dryness. Add toluene (2500 mL) to the residue and then add n-heptane (7500 mL) slowly. Stir for 16 hours. Collect the resulting solids by filtration and wash with n-heptane (1200 mL). Dry the solid under vacuum to obtain the title compound (1075.7 g, 98%).

Preparation 3

1-(5-Bromo-2-fluoro-phenyl)-2-[(1S)-1-(trityloxymethyl)allyloxy]ethanone

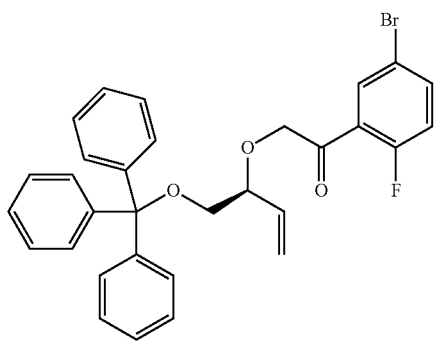 [SMILES: C=C[C@@H](COC(c1ccccc1)(c1ccccc1)c1ccccc1)OCC(=O)c1cc(Br)ccc1F]

Scheme 1a, step B: Add a 1.3 M solution of isopropyl magnesium chloride lithium chloride complex (3079 mL, 2000 mmol) in THF to a solution of 4-bromo-1-fluoro-2-iodobenze (673.2 g, 2237.5 mmol) in toluene (2500 mL) at a rate to maintain the reaction temperature below 5° C. Stir for 1 hour. Add the resulting Grignard solution (5150 mL) to a solution of 1-morpholino-2-[(1S)-1-(trityloxymethyl)allyloxy]ethanone (500 g, 1093 mmol) in toluene (5000 mL) at a rate to maintain the reaction temperature below 5° C. Stir for 3 hours maintaining the temperature below 5° C. Add additional prepared Grignard solution (429 mL) and stir for 1 hour. Add a 1 N aqueous citric acid solution (5000 mL) at a rate to maintain the temperature below 5° C. Separate the layers and wash the organic extract with water (5000 mL). Concentrate the solution under reduced pressure to dryness. Add methanol (2000 mL) to the residue and concentrate to give the title compound as a residue (793 g, 73.4% potency, 83%).

Preparation 4

1-(5-Bromo-2-fluoro-phenyl)-2-[(1S)-1-(trityloxymethyl)allyloxy]ethanone oxime

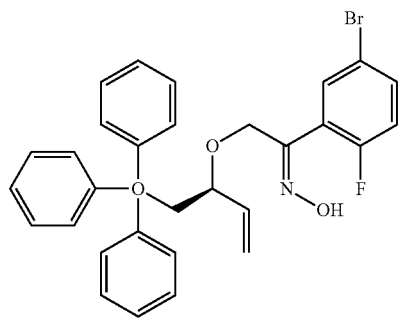

Scheme 1a, step C: Add hydroxylamine hydrochloride (98.3 g) to 1-(5-bromo-2-fluoro-phenyl)-2-[(1S)-1-(trityloxymethyl)allyloxy]ethanone (450 g, 707 mmol) and sodium acetate (174 g) in methanol (3800 mL). Heat the solution to 50° C. for 2 hours. Cool to 24° C. and concentrate. Add water (1000 mL) and toluene (1500 mL) to the residue. Separate the layers and extract the aqueous phase with toluene (500 mL). Combine the organic extract and wash with water (2×400 mL). Concentrate the solution under reduced pressure to give the title compound as a residue (567 g, 61.4% potency, 88%).

Preparation 5 tert-Butyl 2-[(1S)-1-(trityloxymethyl)allyloxy]acetate

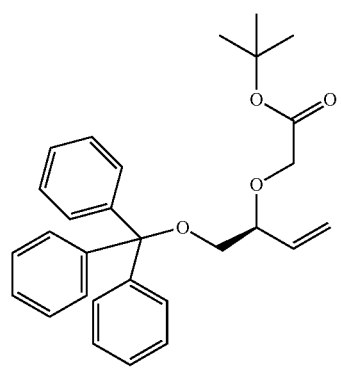 [SMILES: C=C[C@@H](COC(c1ccccc1)(c1ccccc1)c1ccccc1)OCC(=O)OC(C)(C)C]

Scheme 1, step B: Add (2S)-1-trityloxybut-3-en-2-ol (74.67 g, 226.0 mmol) to a solution of tetra-N-butylammonium sulfate (13.26 g, 22.6 mmol) in toluene (376 mL). Add sodium hydroxide (50% mass) in water (119 mL) followed by tert-butyl-2-bromoacetate (110.20 g, 565.0 mmol). Stir reaction mixture for 18 hours at ambient temperature. Pour into water, separate the phases, and extract the aqueous phase with ethyl acetate. Combine the organic layers and dry over magnesium sulfate. Filter the mixture and concentrate under reduced pressure to give the title compound (77.86 g, 77%). ES/MS m/z 467 (M+Na).

Preparation 6

(1E)-2-[(1S)-1-(Trityloxymethyl)allyloxy]acetaldehyde oxime

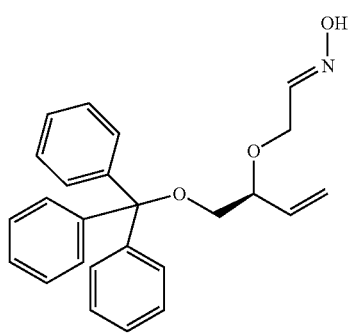 [SMILES: C=C[C@@H](COC(c1ccccc1)(c1ccccc1)c1ccccc1)OC/C=N/O]

Scheme 1, step C: Cool a solution of tert-butyl 2-[(1S)-1-(trityloxymethyl)allyloxy]acetate (77.66 g, 174.7 mmol) in dichloromethane (582.2 mL) to −78° C. Add a solution of diisobutylaluminum hydride in hexanes (1 mol/L, 174.7 mL) dropwise over a period of 35 minutes and maintain the temperature below −70° C. Stir at −78° C. for 5 hours. Add hydrochloric acid in water (2 mol/L, 192.1 mL) to the reaction mixture dropwise, keeping the temperature below −60° C. Allow the reaction to gradually warm to ambient temperature and stir for 60 minutes. Separate the organic extract and wash with saturated sodium bicarbonate. Dry the solution over magnesium sulfate, filter, and concentrate under reduced pressure to give a residue. Dissolve the residue in dichloromethane. Add sodium acetate (28.66 g, 349.3 mmol), followed by hydroxylamine hydrochloride (18.21 g, 262.0 mmol). Stir at ambient temperature for 18 hours. Pour into water, separate the phases, and extract the aqueous phase with dichloromethane. Combine the organic layers and dry over magnesium sulfate. Filter the mixture and concentrate under reduced pressure to give the title compound (68.38 g, 101%). ES/MS m/z 386 (M−H).

Preparation 7

(3aR,4S)-4-(Trityloxymethyl)-3,3a,4,6-tetrahydrofuro[3,4-c]isoxazole

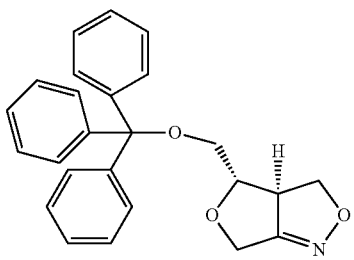 [SMILES: c1ccc(C(OC[C@H]2OCC3=NOC[C@@H]32)(c2ccccc2)c2ccccc2)cc1]

Scheme 1, step D: Cool a solution of (1E)-2-[(1S)-1-(trityloxymethyl)allyloxy]acetaldehyde oxime (55.57 g, 143.4 mmol) in tert-butyl methyl ether (717 mL) to 5° C. Add sodium hypochlorite (5% in water, 591 mL, 430.2 mmol) dropwise, keeping the temperature below 10° C. Stir at 10° C. for 30 minutes. Allow the reaction to warm to 15° C. Stir at 15° C. for 18 hours. Dilute the reaction mixture with ethyl acetate and wash with saturated sodium bicarbonate. Separated the phases, wash the organic phase with a 5% sodium hydrogen sulphite solution and brine. Dry the solution over magnesium sulfate, filter, and concentrate under reduced pressure to give a residue. Purify the residue by silica gel chromatography, eluting with 50% methyl tert-butyl ether/dichloromethane:hexanes (20-27% gradient), to give the title compound (35.84 g, 65%). ES/MS m/z 408 (M+Na).

Preparation 8

(3aR,4S,6aR)-6a-(5-Bromo-2-fluoro-phenyl)-4-(trityloxymethyl)-3,3a,4,6-tetrahydrofuro[3,4-c]isoxazole

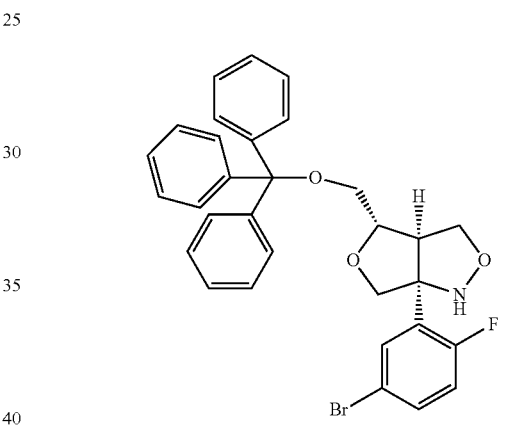

Scheme 1, step E: Cool a solution of 4-bromo-1-fluoro-2-iodo-benzene (86.94 g, 288.9 mmol) in THF (144.5 mL) and toluene (1445 mL) to −78° C. Add n-butyllithium (2.5 M in hexanes, 120 mL, 288.9 mmol) dropwise, keeping the temperature below −70° C. Stir for 30 minutes at −78° C. Add boron trifluoride diethyl etherate (36.5 mL, 288.9 mmol) dropwise, keeping temperature below −70° C. Stir the solution for 30 minutes at −78° C. Add a solution of (3aR,4S)-4-(trityloxymethyl)-3,3a,4,6-tetrahydrofuro[3,4-c]isoxazole (55.69 g, 144.5 mmol) in THF (482 mL) dropwise to the reaction, over a period of 30 minutes, keeping temperature below −65° C. Stir at −78° C. for 90 minutes. Rapidly add saturated ammonium chloride, keeping temperature below −60° C. Pour into brine, and extract the aqueous phase with ethyl acetate. Combine the organic extract and dry over magnesium sulfate. Filter and concentrate under reduced pressure to give a residue. Purify the residue by silica gel chromatography, eluting with a gradient of 100% hexanes to 30% hexanes/70% diethyl ether, to give the title compound (36.52 g, 45%). ES/MS m/e ($^{79}$Br/$^{81}$Br) 560/562 [M+H].

Alternate Preparation 8

Scheme 1a, step D: Heat a solution of 1-(5-bromo-2-fluoro-phenyl)-2-[(1S)-1-(trityloxymethyl)allyloxy]ethanone oxime (458 g, 502 mmol) and hydroquinone (56.3 g 511 mmol) in toluene (4000 mL) to reflux under nitrogen for 27 hours. Cool the solution to 24° C. and add aqueous sodium carbonate (800 mL). Separate the layers and extract the aqueous phase with toluene (300 mL). Combine the organic extract and wash with water (2×500 mL). Concentrate the solution under reduced pressure to give a residue. Add isopropyl alcohol (1500 mL) and heat to reflux. Cool to 24° C. and collect the solids by filtration. Dry the solid under vacuum to obtain the title compound (212 g, 75%).

Preparation 9

1-[(3aR,4S,6aS)-6a-(5-Bromo-2-fluoro-phenyl)-4-(trityloxymethyl)-3,3a,4,6-tetrahydrofuro[3,4-c]isoxazol-1-yl]ethanone

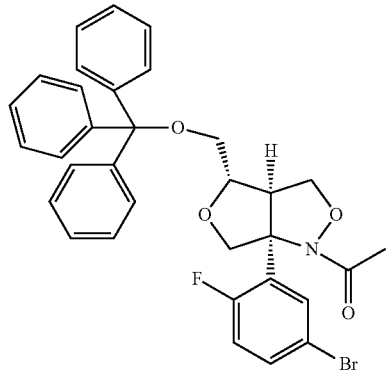 [SMILES: CC(=O)N1OC[C@@H]2[C@@H](COC(c3ccccc3)(c3ccccc3)c3ccccc3)OC[C@@]21c1cc(Br)ccc1F]

Scheme 1a, step E: Add acetyl chloride (35.56 g, 503.9 mmol) to a solution of (3aR,4S,6aR)-6a-(5-bromo-2-fluoro-phenyl)-4-(trityloxymethyl)-3,3a,4,6-tetrahydrofuro[3,4-c]isoxazole (235.3 g, 420 mmol), DMAP (5.13 g, 42.0 mmol), and pyridine (66.45 g, 840.1 mmol) in dichloromethane (720 mL) under nitrogen, maintaining internal temperature below 5° C. Stir for 1 hour and then add water (300 mL) and 1 M sulfuric acid (300 mL). Stir the mixture for 10 minutes and allow the layers to separate. Collect the organic extract and wash with saturated sodium carbonate (500 mL) and water (500 mL). Dry the solution over magnesium sulfate. Filter and concentrate under reduced pressure to give 1-[(3aR,4S,6aS)-6a-(5-Bromo-2-fluoro-phenyl)-4-(trityloxymethyl)-3,3a,4,6-tetrahydrofuro[3,4-c]isoxazol-1-yl]ethanone (235 g, 93%) as a grey solid.

Preparation 10

1-[(3aR,4S,6aS)-6a-(5-Bromo-2-fluorophenyl)-4-(hydroxymethyl)tetrahydro-1H,3H-furo[3,4-c][1,2]oxazol-1-yl]ethanone

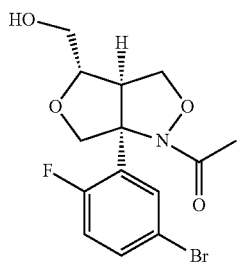 [SMILES: CC(=O)N1OC[C@@H]2[C@@H](CO)OC[C@@]21c1cc(Br)ccc1F]

Scheme 2, step A: In a 20 L jacketed reactor add acetyl chloride (290 mL, 4075 mmol) to a solution of (3aR,4S,6aR)-6a-(5-bromo-2-fluoro-phenyl)-4-(trityloxymethyl)-3,3a,4,6-tetrahydrofuro[3,4-c]isoxazole (1996 g, 3384 mmol), DMAP (56.0 g, 458 mmol), pyridine (500 mL, 6180 mmol) in dichloromethane (10 L) under nitrogen maintaining internal temperature below 10° C. After complete addition (1 hour) warm to 20° C. and stir overnight. If reaction is incomplete, add acetyl chloride, DMAP, pyridine, and dichloromethane until complete reaction is observed. Cool the reaction mixture to 0° C. and slowly add water (5 L), stir the reaction mixture at 10° C. for 30 minutes and allow the layers to separate. Collect the organic extract and wash the aqueous with dichloromethane (1 L). Wash the combined organic extracts with 1 N aqueous hydrochloric acid (2×4 L), extract the aqueous with dichloromethane (2×1 L). Wash the combined organic extracts with water (4 L) and remove the solvent under reduced pressure give total volume of approximately 5 L. Add 90% formic acid (1800 mL) and stand at ambient temperature for 3 days. Warm to 40° C. for 2 hours then remove the solvent under reduced pressure. Dilute the residue with methanol (4 L) and slowly add saturated aqueous sodium carbonate (3 L). Add solid sodium carbonate (375 g) to adjust the pH to 8-9. Stir at 45° C. for 1 hour then cool to ambient temperature. Remove the solids by filtration, washing with methanol (4×500 mL) then treat with 2 N aqueous sodium hydroxide (100 mL) and stand at ambient temperature for 1 hour. Remove the solids by filtration, washing with methanol (2×100 mL). Evaporate the solvent under reduced pressure and partition the residue between ethyl acetate (5 L) and water (2 L). Extract the aqueous with ethyl acetate (2 L) and wash the combined organic extracts with brine (2×1 L). Remove the solvent under reduced pressure, add methyl tert-butyl ether (2.5 L) and evaporate to dryness. Add methyl tert-butyl ether (4 L) and stir at 65° C. for 1 hour cool to ambient temperature and collect the solids by filtration, washing with methyl tert-butyl ether (3×500 mL). Dry under vacuum to a beige solid. Heat this solid in toluene (7.5 L) to 110° C. until fully dissolved, cool to 18° C. over 1 hour, and stir at this temperature for 1 hour. Warm to 40° C. and when precipitate forms, cool to 18° C. once more. Stir for 45 minutes then collect solids by filtration, washing with toluene (2×500 mL). Dry the solid under vacuum to obtain the title compound (443.1 g, 36%, 95% purity by LCMS). Evaporate the filtrate under vacuum to give a residue. Purify the residue by silica gel flash chromatography, eluting with 20% to 100% ethyl acetate in isohexane. Slurry the product containing fractions in methyl tert-butyl ether (2 L) at 60° C. for 30 minutes, cool to ambient temperature, and collect the solids by filtration, washing with methyl tert-butyl ether (2×200 mL). Dry the solids under vacuum to give the title compound as a beige crystalline solid (304 g, 24%, 88% purity by LCMS). Evaporate the filtrate under vacuum to a residue. Purify the residue by silica gel flash chromatography, eluting with 20% to 100% ethyl acetate in isohexane to give the title compound (57.8 g, 5%, 88% purity by LCMS). ES/MS: m/z ($^{79}$Br/$^{81}$Br) 360.0/362.0 [M+H].

Alternate Preparation 10

Scheme 2, step A: Add 1-[(3aR,4S,6aS)-6a-(5-bromo-2-fluoro-phenyl)-4-(trityloxymethyl)-3,3a,4,6-tetrahydrofuro[3,4-c]isoxazol-1-yl]ethanone (69 g, 114.5 mmol) to a 15° C. solution of p-toluenesulfonic acid monohydrate (2.2 g, 11.45 mmol), dichloromethane (280 mL) and methanol (700 mL). Stir for 18 hours and then remove the solvent under reduced pressure. Dilute the residue with dichloromethane (350 mL) and add 1 M aqueous sodium carbonate (140 mL) and water (140 mL). Separate the layers and evaporate the organic layer under reduced pressure. Add toluene (350 mL) to the residue and heat to reflux for 1 hour. Cool to 10-15° C. at a rate of 10° C./hour.

Collect the solids by filtration and wash with toluene (70 mL). Dry the solid under vacuum to obtain the title compound (30 g, 65%) as a grey solid.

Preparation 11

(3aR,4S,6aS)-1-Acetyl-6a-(5-bromo-2-fluoro-phenyl)-3,3a,4,6-tetrahydrofuro[3,4-c]isoxazole-4-carboxylic acid

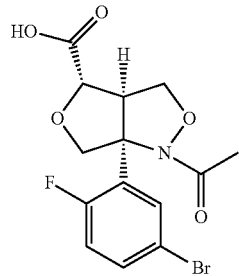

Scheme 2, step B: Add water (2 L) to a suspension of 1-[(3aR,4S,6aS)-6a-(5-bromo-2-fluorophenyl)-4-(hydroxymethyl)tetrahydro-1H,3H-furo[3,4-c][1,2]oxazol-1-yl]ethanone (804.9 g, 2177 mmol), (2,2,6,6-tetramethylpiperidin-1-yl)oxyl (40.0 g, 251 mmol) in acetonitrile (4.5 L) in a 20 L jacketed reactor and cool to an internal temperature of 5° C. Add (diacetoxyiodo)benzene (1693 g, 4993.43 mmol) portionwise over 30 minutes. Control the exotherm using reactor cooling and then hold at 20° C. until LCMS shows complete reaction. Slowly add a suspension of sodium bisulfite (70 g, 672.68 mmol) in water (300 mL) at ambient temperature, maintaining the internal temperature below 25° C. Stir for 30 minutes and then cool to 5° C. Add water (2 L), then slowly add 47 wt % aqueous sodium hydroxide (780 mL) over a period of 1 hour maintaining the internal temperature below 10° C. Add ethyl acetate (2 L) and isohexane (5 L), stir vigorously and separate the layers. Extract the biphasic organic layers with water (1 L) and wash the combined aqueous with methyl tert-butyl ether (2.5 L). Cool the aqueous extracts to 5° C. and slowly add 37% hydrochloric acid (1.4 L) over 30 minutes maintaining the internal temperature around 5° C. Add ethyl acetate (5 L), separate the layers and wash the organic with brine (3×1 L). Extract the combined aqueous extracts with ethyl acetate (2.5 L), wash the combined organics with brine (1 L), then dry with sodium sulfate, and filter. Dilute the organics with heptane (2.5 L) and evaporate to dryness under reduced pressure. Add methyl tert-butyl ether (1.5 L) and heptane (1.5 L) and evaporate to dryness. Add heptane (2.5 L) and evaporate to dryness twice. Add heptane (500 mL) and methyl tert-butyl ether (500 mL) and stir at 40° C. for 30 minutes then collect the precipitate by filtration, washing with heptane/methyl tert-butyl ether (1:1, 1 L) then methyl tert-butyl ether (3×300 mL) and air dry to give the title compound as a beige crystalline solid (779 g, 91%). ES/MS: m/z ($^{79}$Br/$^{81}$Br) 374.0/376.0 [M+H]. $[\alpha]_D^{20}$=−19.0° (C=1.004, chloroform).

Alternate Preparation 11

Scheme 2, step B: Add water (150 mL) and acetonitrile (150 mL) to 1-[(4S,6aS)-6a-(5-bromo-2-fluoro-phenyl)-4-(hydroxymethyl)-3,3a,4,6-tetrahydrofuro[3,4-c]isoxazol-1-yl]ethanone (30 g, 73.3 mmol), TEMPO (1.14 g, 7.30 mmol) and (diacetoxyiodo) benzene (51.9 g, 161 mmol). Cool to 15° C. and stir for 2 hours. Slowly add sodium thiosulfate (21 g) and potassium carbonate (22 g) in water (150 mL) at ambient temperature. Stir for 1 hour and then add methyl tert-butyl ether (150 mL). Separate the layers and adjust the pH of the aqueous layer to 2-3 with concentrated sulfuric acid. Add ethyl acetate (150 mL) and separate the layers. Evaporate the organic layer to dryness under reduced pressure. Add n-heptane (90 mL) and heat to reflux for 1 hour. Cool to 15° C. and then collect the precipitate by filtration, washing with n-heptane (90 mL). Dry under vacuum to give the title compound as a white solid (27 g, 98%).

Preparation 12

(3aR,4S,6aS)-1-Acetyl-6a-(5-bromo-2-fluorophenyl)-N-methoxy-N-methyltetrahydro-1H,3H-furo[3,4-c][1,2]oxazole-4-carboxamide

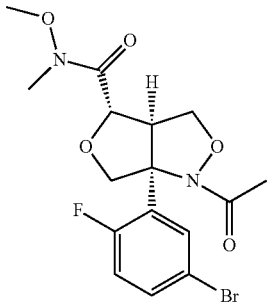 [SMILES: CON(C)C(=O)[C@H]1OC[C@@]2(c3cc(Br)ccc3F)[C@@H]1CON2C(C)=O]

Scheme 2, step C: In a 10 L jacketed reactor, cool a solution of (3aR,4S,6aS)-1-acetyl-6a-(5-bromo-2-fluoro-phenyl)-3,3a,4,6-tetrahydrofuro[3,4-c]isoxazole-4-carboxylic acid (771 g, 2019 mmol) in dichloromethane (7.0 L) to 0° C. under nitrogen and add CDI (400 g, 2421 mmol) portionwise over 40 minutes. Cool the reactor jacket to −20° C. and stir for 1 hour and then add N,O-dimethylhydroxylamine hydrochloride (260.0 g, 2612 mmol) portionwise over about 30 minutes. Stir at −20° C. for 1 hour, at 0° C. for 2 hours, and at 10° C. for 7 hours. Add CDI (175 g, 1058 mmol) and stir at 10° C. overnight. Add further CDI (180 g, 1088 mmol) at 10° C. and stirred for 1 hour then add N,O-dimethylhydroxylamine hydrochloride (140 g, 1407 mmol) and continue stirring at 10° C. If the reaction is incomplete, further charges of CDI followed by N,O-dimethylhydroxylamine hydrochloride can be made until complete reaction is observed. Cool the reaction mixture to 5° C. and wash with 1 N aqueous hydrochloric acid (5 L) then 2 N aqueous hydrochloric acid (5 L). Extract the combined aqueous solution with dichloromethane (1 L), combine the organic extract and wash with water (2.5 L), 1 N aqueous sodium hydroxide (2.5 L), and water (2.5 L), dry over magnesium sulfate, filter, and evaporate under reduced pressure to give a residue. Add methyl tert-butyl ether (3 L) and evaporate under reduced pressure. Add further methyl tert-butyl ether (2 L) and stir at 50° C. for 1 hour, cool to 25° C. and stir for 30 minutes. Collect the resulting solids by filtration, wash with methyl tert-butyl ether (2×500 mL) and dry under vacuum to give the title compound (760 g, 88%) as a white solid. ES/MS: m/z ($^{79}$Br/$^{81}$Br) 417.0/419.0 [M+H].

Alternate Preparation 12

Scheme 2, step C: Cool a solution of (3aR,4S,6aS)-1-acetyl-6a-(5-bromo-2-fluoro-phenyl)-3,3a,4,6-tetrahydrofuro[3,4-c]isoxazole-4-carboxylic acid (27 g, 70.7 mmol) in N,N-dimethylformamide (135 mL) to 0° C. under nitrogen and add CDI (14.9 g, 91.9 mmol). Stir for 1 hour and then add N,O-dimethylhydroxylamine hydrochloride (9.0 g, 92 mmol) and triethylamine (14.3 g, 141 mmol). Stir at 15° C. for 16 hours. Cool the reaction mixture to 0° C. and add 0.5 M aqueous sulfuric acid (675 mL). Stir for 1 hour. Collect the resulting solids by filtration. Slurry the solids in methyl tert-butyl ether (90 mL) for 1 hour. Collect the solids by filtration, wash with methyl tert-butyl ether (30 mL). Dry under vacuum to give the title compound (23 g, 78%) as a solid.

Preparation 13

1-[(3aR,4S,6aS)-1-Acetyl-6a-(5-bromo-2-fluoro-phenyl)-3,3a,4,6-tetrahydrofuro[3,4-c]isoxazol-4-yl]ethanone

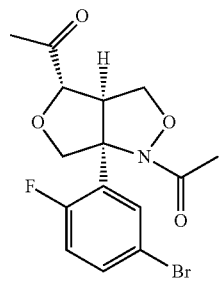 [SMILES: CC(=O)[C@H]1OC[C@@]2(c3cc(Br)ccc3F)[C@@H]1CON2C(C)=O]

Scheme 2, step D: In a 20 L jacketed reactor, cool a solution of (3aR,4S,6aS)-1-acetyl-6a-(5-bromo-2-fluoro-phenyl)-N-methoxy-N-methyltetrahydro-1H,3H-furo[3,4-c][1,2]oxazole-4-carboxamide (654.0 g, 1536 mmol) in THF (10 L) to −60° C. and add a 3.2 M solution of methylmagnesium bromide in 2-methyltetrahydrofuran (660 mL, 2110 mmol) dropwise, while maintaining the internal temperature below −40° C. Stir the reaction mixture at −40° C. for 30 minutes then cool to −50° C. and add a solution of 1 N aqueous hydrochloric acid (2 L) in THF (2 L) maintaining the internal temperature below −38° C. Increase the temperature to 10° C. and add ethyl acetate (5 L) and water (1 L), stir and allow internal temperature to reach 5° C. and separate the layers. Extract the aqueous layer with ethyl acetate (1 L) and combine the organic extracts. Wash the organic extracts with water (2 L) and extract the aqueous layer with ethyl acetate (1 L). Combine the organic extract and wash with brine (3×2 L) then dry over magnesium sulfate, filter, and evaporate under reduced pressure to a residue. Add cyclohexane (2.5 L), stir at 60° C. for 1 hour then at 20° C. for 30 minutes, and collect the solid by filtration, washing with cyclohexane (500 mL). Dry the solid under vacuum to obtain the title compound as a white solid (565 g, 99%). ES/MS: m/z ($^{79}$Br/$^{81}$Br) 372.0/374.0 [M+H], [α]$_D^{20}$=−58.0° (C=1.000, chloroform).

Alternate Preparation 13

Scheme 2, step D: Cool a solution of (3aR,4S,6aS)-1-acetyl-6a-(5-bromo-2-fluorophenyl)-N-methoxy-N-methyltetrahydro-1H,3H-furo[3,4-c][1,2]oxazole-4-carboxamide (4.0 g, 9.59 mmol) in THF (60 mL) to −5° C. and add a 3.0 M solution of methylmagnesium bromide in 2-methyltetrahydrofuran (5.0 mL, 15 mmol) dropwise, while maintaining the internal temperature between −5 and 0° C. Stir the reaction mixture between −5 and 0° C. for 60 minutes then add a solution of saturated ammonium chloride (20 mL). Add methyl tert-butyl ether (40 mL), allow the internal temperature to reach 5° C. and separate the layers. Evaporate the organic layer under reduced pressure to a residue. Add n-heptane (50 mL), stir, and collect the solid by filtration. Dry the solid under vacuum to obtain the title compound as a solid (3.0 g, 77%).

Preparation 14

1-[(3aR,4S,6aS)-6a-(5-Bromo-2-fluorophenyl)-4-(1,1-difluoroethyl)tetrahydro-1H,3H-furo[3,4-c][1,2]oxazol-1-yl]ethanone

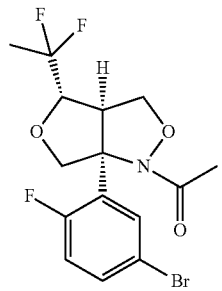 [SMILES: CC(=O)N1OC[C@@H]2[C@@H](C(C)(F)F)OC[C@@]21c1cc(Br)ccc1F]

Scheme 2, step E: Add 1-[(3aR,4S,6aS)-1-acetyl-6a-(5-bromo-2-fluoro-phenyl)-3,3a,4,6-tetrahydrofuro[3,4-c]isoxazol-4-yl]ethanone (5.08 g, 13.6 mmol) in a single portion to a stirred suspension of difluoro(morpholino)sulfonium tetrafluoroborate (10.02 g, 39.18 mmol) in anhydrous dichloromethane (100 mL) at 0-5° C. Stir the mixture for 10 minutes and add triethylamine trihydrofluoride (4.5 mL, 27 mmol) dropwise over 10 minutes. Stir the reaction mixture in the ice-bath for 8 hours then warm to ambient temperature and stir overnight. Add saturated aqueous sodium carbonate (100 mL) and stir for 1 hour. Separate the layers and extract the aqueous with dichloromethane (2×50 mL). Combine the organic extracts and wash with saturated aqueous sodium bicarbonate (100 mL), 2 N aqueous hydrochloric acid (2×100 mL), and brine (100 mL). Evaporate to dryness to a light brown solid and dissolve in methyl tert-butyl ether (300 mL) at 60° C. Filter the hot solution and evaporate the filtrate to give a brown solid (5.3 g, 81%, 82% purity by LCMS) that is used without further purification. ES/MS: m/z ($^{79}$Br/$^{81}$Br) 393.8/395.8 [M+H].

Alternate Preparation 14

Scheme 2, step E: Add XtalFluor-M® (1.21 kg, 4.73 mol) in portions to a stirred solution of 1-[(3aR,4S,6aS)-1-acetyl- 6a-(5-bromo-2-fluoro-phenyl)-3,3a,4,6-tetrahydrofuro[3,4-c]isoxazol-4-yl]ethanone (565 g, 1.51 mol) in anhydrous dichloromethane (5 L) at −14° C. Stir the mixture for 10 minutes and add triethylamine trihydrofluoride (550 g, 3.34 mol) dropwise over 20 minutes. Stir the reaction mixture at −10° C. for approximately 10 hours then warm to ambient temperature and stir overnight. Add 50% aqueous sodium hydroxide (750 mL) slowly, maintaining the internal temperature below 10° C., then add water (1.5 L) and saturated aqueous sodium hydrogen carbonate (1 L) and stir for 30 minutes. Separate the layers and extract the aqueous with dichloromethane (1 L). Combine the organic extracts and wash with brine (3 L), 2 N aqueous hydrochloric acid (5 L), and brine (3 L). Evaporate to give a residue and purify by silica gel chromatography eluting with 50-100% dichloromethane in iso-hexane then 10% methyl tert-butyl ether in dichloromethane to give the title compound as a white powder (467 g, 73%, 94% purity by LCMS). ES/MS: m/z ($^{79}$Br/$^{81}$Br) 393.8/395.8 [M+H].

Preparation 15

(3 aR,4S,6aS)-6a-(5-Bromo-2-fluoro-phenyl)-4-(1,1-difluoroethyl)-3,3a,4,6-tetrahydro-1H-furo[3,4-c]isoxazole

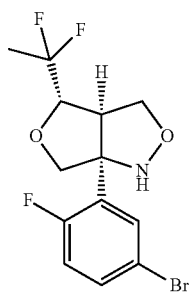 [SMILES: CC(F)(F)[C@H]1OC[C@]2(c3cc(Br)ccc3F)NOC[C@H]12]

Scheme 2, step F: Add 37 wt % aqueous hydrochloric acid (1.3 L, 16 mol) to a solution of 1-[(3aR,4S,6aS)-6a-(5-bromo-2-fluorophenyl)-4-(1,1-difluoroethyl)tetrahydro-1H,3H-furo[3,4-c][1,2]oxazol-1-yl]ethanone (570 g, 1.45 mol) in 1,4-dioxane (5 L) in a 10 L jacketed reactor and stir at 100° C. for approximately 3 hours or until LCMS shows complete reaction. Cool the reaction mixture to 10° C., dilute with water (1 L) and add a mixture 50 wt % aqueous sodium hydroxide solution (800 mL) and water (1 L) slowly, maintaining the internal temperature below 20° C. Add ethyl acetate (2.5 L) and stir vigorously, before separating the layers and washing the organic phase with brine (2 L), further brine (1 L), and water (1 L). Dry over magnesium sulfate, filter and concentrate to dryness under reduced pressure to give a residue. Add cyclohexane (2.5 L) and evaporate to dryness then repeat to obtain the title compound as a brown oil (527 g, 89%, 86% purity by LCMS). ES/MS: m/z ($^{79}$Br/$^{81}$Br) 351.8/353.8 [M+H].

Preparation 16

[(2S,3R,4S)-4-Amino-4-(5-bromo-2-fluorophenyl)-2-(1,1-difluoroethyl)tetrahydrofuran-3-yl]methanol

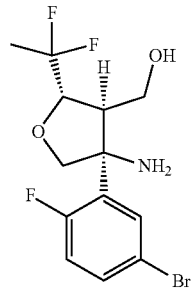

Scheme 2, step G: Add zinc powder (6.0 g, 92 mmol) to a solution of (3aR,4S,6aS)-6a-(5-bromo-2-fluoro-phenyl)-4-(1,1-difluoroethyl)-3,3a,4,6-tetrahydro-1H-furo[3,4-c]isoxazole (5.06 g, 13.4 mmol) in acetic acid (100 mL) at ambient temperature and stir overnight. Dilute the mixture with ethyl acetate (200 mL) and water (300 mL) and stir vigorously while adding sodium carbonate (97 g, 915 mmol). Separate the layers and wash the organic layer with brine (2×200 mL), dry over magnesium sulfate, filter, and concentrate to give a residue. Purify the residue by silica gel chromatography eluting with 0% to 100% methyl tert-butyl ether in iso-hexane to give the title compound as a waxy solid (4.67 g, 89%, 90% purity by LCMS). ES/MS: m/z ($^{79}$Br/$^{81}$Br) 354.0/356.0 [M+H].

Alternate Preparation 16

Scheme 2, step G: Add zinc powder (200 g, 3.06 mol) portionwise to a solution of (3aR,4S,6aS)-6a-(5-bromo-2-fluoro-phenyl)-4-(1,1-difluoroethyl)-3,3a,4,6-tetrahydro-1H-furo[3,4-c]isoxazole (304 g, 75% purity, 647 mmol) in acetic acid (2 L) and water (2 L) at 20° C. then warm to 40° C. and stir overnight. Dilute the mixture with water (2 L) and stir vigorously while adding sodium carbonate (4 kg, 43.4 mol) then adjust to pH 8-9 with further sodium carbonate. Add ethyl acetate (5 L) and water (2.5 L), stir for 30 minutes and filter through diatomaceous earth washing with 2:1 acetonitrile/water. Separate the layers, extract the aqueous with ethyl acetate (2×2.5 L) and wash the combined organic extracts with brine (2×2.5 L), dry over magnesium sulfate, filter, and concentrate to give a residue. Purify the residue by SFC, column: Chiralpak AD-H (5), 50×250 mm; eluent: 12% ethanol (0.2% diethylmethylamine in $CO_2$; flow rate: 340 g/minute at UV 220 nm to give the title compound as a white solid (197.7 g, 84%). $[\alpha]_D^{20}$=−6.93° (C=0.678, chloroform). ES/MS: m/z ($^{79}$Br/$^{81}$Br) 354.0/356.0 [M+H].

Preparation 17

[(2S,3R,4S)-4-Amino-4-(5-bromo-2-fluoro-phenyl)-2-(trityloxymethyl)tetrahydrofuran-3-yl]methanol

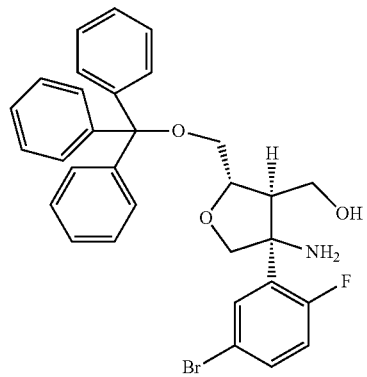 [SMILES: N[C@@]1(c2cc(Br)ccc2F)CO[C@H](COC(c2ccccc2)(c2ccccc2)c2ccccc2)[C@H]1CO]

Scheme 1, step F: Add (3aR,4S,6aR)-6a-(5-bromo-2-fluoro-phenyl)-4-(trityloxymethyl)-3,3a,4,6-tetrahydrofuro[3,4-c]isoxazole (31.30 g, 55.9 mmol) to acetic acid (186 mL) to give a suspension. Add zinc (25.6 g, 391 mmol) and stir the reaction mixture vigorously for 18 hours. Dilute the mixture with toluene and filter through diatomaceous earth. Concentrate the filtrate under reduced pressure. Solubilize the residue with ethyl acetate, wash with brine, and saturated sodium bicarbonate. Separate the phases, dry over magnesium sulfate, filter, and concentrate under reduced pressure to give the title compound (31.35 g, 99%). ES/MS m/e ($^{79}$Br/$^{81}$Br) 562/564 [M+H].

Preparation 18

N-[[(3S,4R,5S)-3-(5-Bromo-2-fluoro-phenyl)-4-(hydroxymethyl)-5-(trityloxymethyl)tetrahydrofuran-3-yl]carbamothioyl]benzamide

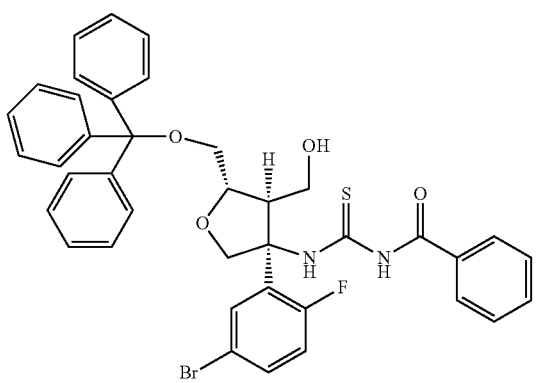 [SMILES: O=C(NC(=S)N[C@@]1(c2cc(Br)ccc2F)CO[C@H](COC(c2ccccc2)(c2ccccc2)c2ccccc2)[C@H]1CO)c1ccccc1]

Scheme 1, step G: Dissolve [(2S,3R,4S)-4-amino-4-(5-bromo-2-fluoro-phenyl)-2-(trityloxymethyl) tetrahydrofuran-3-yl]methanol (31.35 g, 55.73 mmol) in dichloromethane (557 mL) and cool to 5° C. Add benzoyl isothiocyanate (9.74 mL, 72.45 mmol). After addition is complete, allow the reaction mixture to warm to room temperature and stir for 2 hours. Pour into saturated sodium bicarbonate, separate the phases, and extract the aqueous phase with dichloromethane. Combine the organic extract and dry over magnesium sulfate. Filter the solution and concentrate under reduced pressure to give the title compound (42.95 g, 106%). ES/MS m/e ($^{79}$Br/$^{81}$Br) 747/749 [M+Na].

Preparation 19

N-[(4aS,5S,7aS)-7a-(5-Bromo-2-fluoro-phenyl)-5-(1,1-difluoroethyl)-4,4a,5,7-tetrahydrofuro[3,4-d][1,3]thiazin-2-yl]benzamide

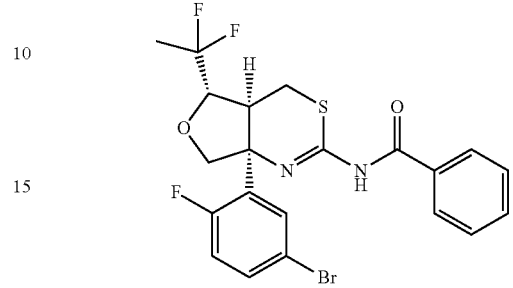

Scheme 2, step H: Add benzoyl isothiocyanate (1.80 mL, 13.3 mmol) to a solution of [(2S,3R,4S)-4-amino-4-(5-bromo-2-fluorophenyl)-2-(1,1-difluoroethyl)tetrahydrofuran-3-yl]methanol (4.67 g, 11.9 mmol) in dichloromethane (20 mL) at ambient temperature for 1 hour until LCMS shows reaction is complete. Evaporate the reaction mixture to a residue under vacuum. Add cyclohexane (50 mL), warm to 60° C. and add methyl tert-butyl ether until precipitate is fully dissolved (100 mL). Filter the hot solution, cool to room temperature and slowly evaporate under reduced pressure until formation of a white precipitate. Remove the solvent under reduced pressure and dissolve the residue in anhydrous dichloromethane (30 mL), add pyridine (2.4 mL, 30 mmol), and cool the solution to −25° C. Add trifluoromethanesulfonic anhydride (2.2 mL 13 mmol) dropwise over 30 minutes and allow to warm 0° C. over 1 hour. Wash the reaction mixture with water (25 mL), 2 N aqueous hydrochloric acid (25 mL), water (25 mL), aqueous saturated sodium bicarbonate (25 mL), and water (25 mL), dry over magnesium sulfate, filter, and concentrated to dryness. Purify the residue by silica gel chromatography eluting with 5% methyl tert-butyl ether in dichloromethane to give the title compound as a light yellow foam (5.0 g, 76%, 90% purity by LCMS). ES/MS: m/z ($^{79}$Br/$^{81}$Br) 499.0/501.0 [M+H].

Alternate Preparation 19

Scheme 2, step H: Add benzoyl isothiocyanate (98 mL, 724.9 mmol) to a solution of [(2S,3R,4S)-4-amino-4-(5-bromo-2-fluorophenyl)-2-(1,1-difluoroethyl)tetrahydrofuran-3-yl]methanol (197.6 g, 546.7 mmol) in dichloromethane (1.2 L) at 30° C. for 1 hour. Add CDI (101 g, 610.4 mmol) and stir at ambient temperature for 3 hours. Further charges of CDI can be made to ensure complete consumption of the thiourea intermediate. Heat to 90° C. for 42 hours and cool the solution to ambient temperature. Dilute the reaction mixture with ethyl acetate (2 L) and add 2 N aqueous hydrochloric acid (2 L), stir, add brine (1 L) and separate the layers. Wash the organic layer with 2 N aqueous hydrochloric acid (0.5 L), brine (2×1 L) and aqueous saturated sodium bicarbonate (1 L). Dry over magnesium sulfate, filter, and concentrate to give a residue. Purify the residue by silica gel chromatography eluting with 0-100% ethyl acetate in iso-hexane to give the title compound as a light yellow solid (234 g, 83%). ES/MS: m/z ($^{79}$Br/$^{81}$Br) 499.0/501.0 [M+H].

Preparation 20

N-[(4aS,5S,7aS)-7a-(5-Bromo-2-fluoro-phenyl)-5-(trityloxymethyl)-4,4a,5,7-tetrahydrofuro[3,4-d][1,3]thiazin-2-yl]benzamide

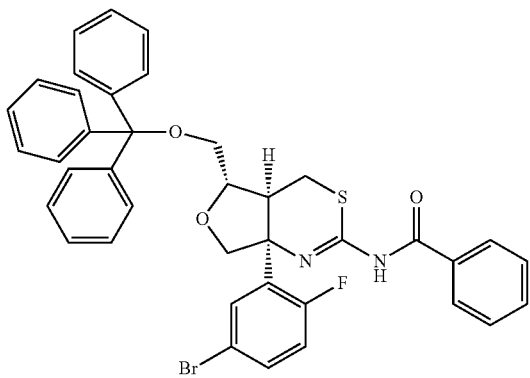 [SMILES: O=C(NC1=N[C@@]2(c3cc(Br)ccc3F)CO[C@H](COC(c3ccccc3)(c3ccccc3)c3ccccc3)[C@H]2CS1)c1ccccc1]

Scheme 1, step H: Dissolve N-[[(3S,4R,5S)-3-(5-bromo-2-fluoro-phenyl)-4-(hydroxymethyl)-5-(trityloxymethyl)tetrahydrofuran-3-yl]carbamothioyl]benzamide (42.95 g, 59.18 mmol) in dichloromethane (591 mL) and cool to −20° C. Add pyridine (12.0 mL, 148.0 mmol), followed by trifluoromethanesulfonic anhydride (10.97 mL, 65.10 mmol). Monitor the addition keeping the temperature below −20° C. Stir the reaction mixture at −20° C. for 30 minutes. Allow the reaction mixture to warm to room temperature. Pour into saturated ammonium chloride, separate the phases, and extract the aqueous phase with dichloromethane. Combine the organic extract and dry over magnesium sulfate. Filter the solution and concentrate under reduced pressure to give the title compound (45.24 g, 108%). ES/MS m/e ($^{79}$Br/$^{81}$Br) 707/709 [M+H].

Preparation 21

N-[(4aS,5S,7aS)-7a-(5-Bromo-2-fluoro-phenyl)-5-(hydroxymethyl)-4,4a,5,7-tetrahydrofuro[3,4-d][1,3]thiazin-2-yl]benzamide

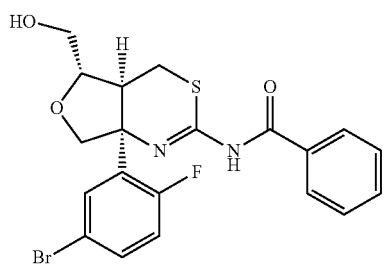 [SMILES: O=C(NC1=N[C@@]2(c3cc(Br)ccc3F)CO[C@H](CO)[C@H]2CS1)c1ccccc1]

Scheme 1, step I: Dissolve N-[(4aS,5S,7aS)-7a-(5-bromo-2-fluoro-phenyl)-5-(trityloxymethyl)-4,4a,5,7-tetrahydrofuro[3,4-d][1,3]thiazin-2-yl]benzamide (45.24 g, 63.93 mmol) in formic acid (160 mL) and stir at ambient temperature for 1 hour. Add water (29 mL) over a period of 5 minutes. Stir for 50 minutes. Concentrate the mixture under reduced pressure to a residue. Dissolve the residue in methanol (639 mL), add triethylamine (26.7 mL, 191.8 mmol), and stir overnight at ambient temperature. Pour into brine, separate the phases, and extract the aqueous phase with chloroform. Combine the organic extract and dry over magnesium sulfate. Filter and concentrate under reduced pressure to give a residue. Purify the residue by silica gel chromatography, eluting with acetone:hexanes (25-38% gradient), to give the title compound (16.04 g, 54%). ES/MS m/e (79Br/81Br) 465/467 [M+H].

Preparation 22

(4aS,5S,7aS)-2-Benzamido-7a-(5-bromo-2-fluoro-phenyl)-4,4a,5,7-tetrahydrofuro[3,4-d][1,3]thiazine-5-carboxylic acid

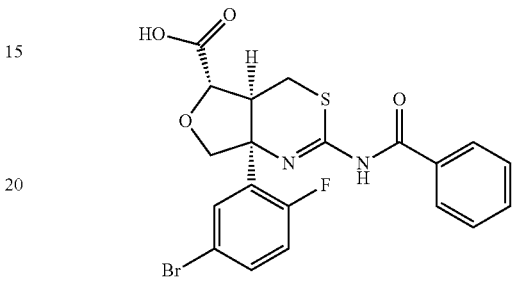

Scheme 1, step J: Add N-[(4aS,5S,7aS)-7a-(5-bromo-2-fluoro-phenyl)-5-(hydroxymethyl)-4,4a,5,7-tetrahydrofuro[3,4-d][1,3]thiazin-2-yl]benzamide (16.04 g, 34.47 mmol) to DMSO (172 mL). Add 2-iodoxybenzoic acid (35.56 g, 120.70 mmol) and stir at ambient temperature for 3 hours. Dilute the reaction mixture with chloroform (300 mL) and pour into saturated ammonium chloride (400 mL). Separate the organic phase and dry over magnesium sulfate. Filter the solution and concentrate under reduced pressure to give a residue. Dissolve the residue in ethyl acetate (400 mL) and wash with saturated ammonium chloride (2×250 mL). Separate the organic phase, dry over magnesium sulfate, filter, and concentrate under reduced pressure to give a residue. Dissolve the residue in a dichloromethane:methanol mixture and add diethyl ether until a solid precipitates. Collect the solid by filtration and dry under reduced pressure to give the title compound (5.78 g, 35%). ES/MS m/e ($^{79}$Br/$^{81}$Br) 479/481 [M+H].

Preparation 23

(4aS,5 S,7aS)-2-Benzamido-7a-(5-bromo-2-fluoro-phenyl)-N-methoxy-N-methyl-4,4a,5,7-tetrahydrofuro[3,4-d][1,3]thiazine-5-carboxamide

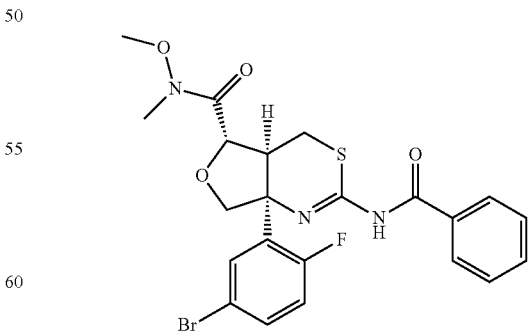

Scheme 1, step K: Dissolve (4aS,5S,7aS)-2-benzamido-7a-(5-bromo-2-fluoro-phenyl)-4,4a,5,7-tetrahydrofuro[3,4-d][1,3]thiazine-5-carboxylic acid (5.78 g, 12.1 mmol) in dichloromethane (201 mL) and N,O-dimethylhydroxylamine hydrochloride (1.76 g, 18.1 mmol). Add triethylamine (5.29 mL, 36.2 mmol) followed by HATU (7.02 g, 18.1 mmol). Stir at ambient temperature for 3 days. Pour into saturated ammonium chloride, separate the phases, and extract the aqueous phase with ethyl acetate. Combine the organic extracts and dry over magnesium sulfate. Filter and concentrate under reduced pressure to give a residue. Purify the residue by silica gel chromatography, eluting with ethyl acetate:dichloromethane (0-50% gradient) to give the title compound (4.15 g, 66%). ES/MS m/e ($^{79}$Br/$^{81}$Br) 522/524 [M+H].

Preparation 24

N-[(4aS,5S,7aS)-5-Acetyl-7a-(5-bromo-2-fluoro-phenyl)-4,4a,5,7-tetrahydrofuro[3,4-d][1,3]thiazin-2-yl]benzamide

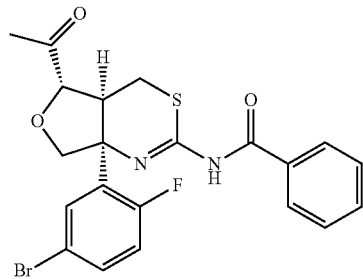 [SMILES: CC(=O)[C@H]1OC[C@]2(c3cc(Br)ccc3F)N=C(NC(=O)c3ccccc3)SC[C@H]12]

Scheme 1, step L: Add dropwise to a −78° C. solution of (4aS,5S,7aS)-2-benzamido-7a-(5-bromo-2-fluoro-phenyl)-N-methoxy-N-methyl-4,4a,5,7-tetrahydrofuro[3,4-d][1,3]thiazine-5-carboxamide (1.51 g, 2.89 mmol) in THF (57.8 mL) methylmagnesium bromide (3.0 mol/L in diethyl ether, 4.8 mL, 14.5 mmol). Stir the reaction at −78° C. for 5 minutes and allow to gradually warm to ambient temperature. Stir for 30 minutes. Quench the reaction with methanol (4 mL), dilute with saturated ammonium chloride, and extract with ethyl acetate. Combine the organic extract and dry over sodium sulfate. Filter and concentrate under reduced pressure to give a residue. Purify the residue by silica gel chromatography, eluting with ethyl acetate:hexanes (0-100% gradient) to give the title compound (1.28 g, 93%). ES/MS m/e ($^{79}$Br/$^{81}$Br) 477/479 [M+H].

Preparation 25

N-[(4aS,5S,7aS)-7a-(5-Bromo-2-fluoro-phenyl)-5-(1,1-difluoroethyl)-4,4a,5,7-tetrahydrofuro[3,4-d][1,3]thiazin-2-yl]benzamide

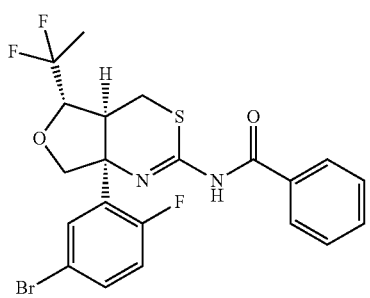 [SMILES: CC(F)(F)[C@H]1OC[C@]2(c3cc(Br)ccc3F)N=C(NC(=O)c3ccccc3)SC[C@H]12]

Scheme 1, step M: Add together dichloromethane (34 mL), bis(2-methoxyethyl)aminosulfur trifluoride (1.52 mL, 6.88 mmol), and boron trifluoride diethyl etherate (0.89 mL, 6.88 mmol). Stir at ambient temperature for 2 hours. Add N-[(4aS,5S,7aS)-5-acetyl-7a-(5-bromo-2-fluoro-phenyl)-4,4a,5,7-tetrahydrofuro[3,4-d][1,3]thiazin-2-yl]benzamide (0.821 g, 1.72 mmol) in one portion, followed by triethylamine trihydrofluoride (1.13 mL, 6.88 mmol). Stir at ambient temperature for 18 hours. Pour into saturated ammonium chloride, separate the phases, and extract the aqueous phase with ethyl acetate. Combine the organic extract and dry over magnesium sulfate. Filter and concentrate under reduced pressure to give a residue. Purify the residue by silica gel chromatography, eluting with dichloromethane:hexanes (80-100% gradient), to give the title compound (0.552 g, 64%). ES/MS m/e ($^{79}$Br/$^{81}$Br) 499/501 [M+H].

Preparation 26

N-[(5S,7aS)-5-(1,1-Difluoroethyl)-7a-{2-fluoro-5-[(trifluoroacetyl)amino]phenyl}-4a,5,7,7a-tetrahydro-4H-furo[3,4-d][1,3]thiazin-2-yl]benzamide

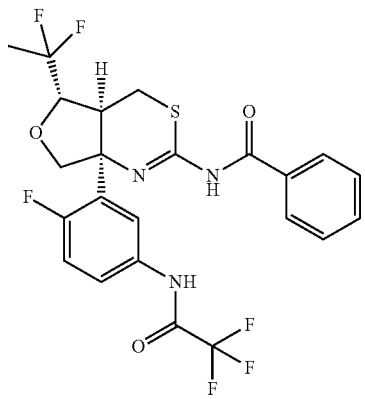 [SMILES: CC(F)(F)[C@H]1OC[C@]2(c3cc(NC(=O)C(F)(F)F)ccc3F)N=C(NC(=O)c3ccccc3)SC[C@H]12]

Scheme 5, step A: Dissolve N-[(4aS,5S,7aS)-7a-(5-bromo-2-fluorophenyl)-5-(1,1-difluoroethyl)-4a,5,7,7a-tetrahydro-4H-furo[3,4-d][1,3]thiazin-2-yl]benzamide (234 g, 454.6 mmol) in 1,4-dioxane (2 L) and add 4 Å molecular sieves (37 g), 2,2,2-trifluoroacetamide (91 g, 780.9 mmol), finely ground potassium carbonate (114 g, 824.9 mmol), sodium iodide (117 g, 780.6 mmol), copper (I) iodide (17.5 g, 91.9 mmol) and racemic trans-N,N'-dimethyl-1,2-cyclohexane diamine (20 g, 140.6 mmol) under a stream of nitrogen. Purge the vessel with 3 vacuum nitrogen switches and heat to 123° C. for 18 hours. Cool to ambient temperature and filter the solution through diatomaceous earth, and wash with ethyl acetate. Add saturated aqueous ammonium chloride (2 L) and vigorously stir for 45 minutes. Separate the layers and wash the organic layer with saturated aqueous ammonium chloride (3×1 L), brine (300 mL), dry over magnesium sulfate, filter, and evaporate to give a residue. Purify the residue by silica gel chromatography eluting with 0-100% ethyl acetate in iso-hexane to give the title compound as a light yellow solid (297.9 g, 95%, 81% purity). ES/MS: m/z 532.0 [M+H].

Preparation 27

N-[(4aS,5S,7aS)-7a-(5-Amino-2-fluoro-phenyl)-5-(1,1-difluoroethyl)-4,4a,5,7-tetrahydrofuro[3,4-d][1,3]thiazin-2-yl]benzamide

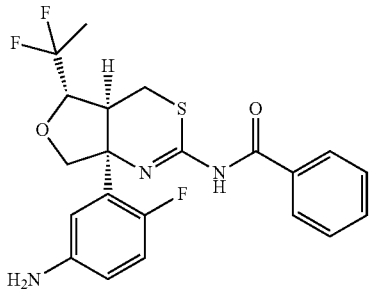 [SMILES: CC(F)(F)[C@H]1OC[C@]2(c3cc(N)ccc3F)N=C(NC(=O)c3ccccc3)SC[C@H]12]

Scheme 1, step N: Combine N-[(4aS,5S,7aS)-7a-(5-bromo-2-fluoro-phenyl)-5-(1,1-difluoroethyl)-4,4a,5,7-tetrahydrofuro[3,4-d][1,3]thiazin-2-yl]benzamide (0.372 g, 0.74 mmol) and (1R,2R)—N,N'-dimethyl-1,2-cyclohexanediamine (0.037 mL, 0.22 mmol) in ethanol (30 ml). Add sodium azide (0.194 g, 2.98 mmol), followed by sodium ascorbate (0.66 M solution, 0.50 ml, 0.33 mmol). Purge the top of the flask with nitrogen and add cupric sulfate (0.33 M solution, 0.68 ml, 0.22 mmol). Heat the reaction mixture to 80° C. and stir for 5 hours. Cool the reaction and add cold water. Extract the mixture with ethyl acetate. Combine the organic extract and dry over sodium sulfate. Filter and concentrate under reduced pressure to give a residue. Combine the residue with palladium (10 mass % on carbon, 0.35 g, 0.16 mmol) in ethanol (50 ml) and THF (10 ml). Purge the mixture with nitrogen and with hydrogen. Stir at ambient temperature under 50 psi of hydrogen for 1 hour. Filter off the catalyst and wash with ethyl acetate. Concentrate the solution under reduced pressure to give a residue. Purify the residue by silica gel chromatography, eluting with ethyl acetate:dichloromethane (0-20% gradient), to give the title compound (0.2184 g, 67%). ES/MS m/z 436 (M+H).

Alternate Preparation 27

Scheme 5, step B: Add 7 N ammonia in methanol (600 mL, 4.2 mol) to a stirred suspension of N-[(5S,7aS)-5-(1,1-difluoroethyl)-7a-{2-fluoro-5-[(trifluoroacetyl)amino]phenyl}-4a,5,7,7a-tetrahydro-4H-furo[3,4-d][1,3]thiazin-2-yl]benzamide (250 g, 80% purity, 376.3 mmol) in methanol (200 mL) at room temperature and stir at ambient temperature for 18 hours. Evaporate to dryness to give the title compound as a brown gum (190 g, 375.2 mmol, 86% purity). ES/MS: m/z 436.0 [M+H].

Preparation 28

(4aS,5S,7aS)-7a-(5-Amino-2-fluorophenyl)-5-(1,1-difluoroethyl)-4a,5,7,7a-tetrahydro-4H-furo[3,4-d][1,3]thiazin-2-amine

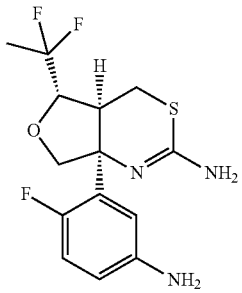 [SMILES: CC(F)(F)[C@H]1OC[C@]2(c3cc(N)ccc3F)N=C(N)SC[C@H]12]

Scheme 4, step A: Dissolve N-[(4aS,5S,7aS)-7a-(5-amino-2-fluoro-phenyl)-5-(1,1-difluoroethyl)-4,4a,5,7-tetrahydrofuro[3,4-d][1,3]thiazin-2-yl]benzamide (216.4 g, 88% purity, 435.9 mmol) in pyridine (400 mL), ethanol (100 mL) and THF (300 mL). Add O-methylhydroxylamine hydrochloride (190 g, 2275.0 mmol) and stir at ambient temperature for 18 hours. Dilute with 2-methyltetrahydrofuran (1 L) and wash with water (2×300 mL). Isolate the organic layer and add 35% aqueous ammonium hydroxide (100 mL) to the aqueous. Extract with 2-methyltetrahydrofuran (300 mL) then saturate with sodium chloride and extract with 2-methyltetrahydrofuran (2×300 mL). Combine the organic extracts, wash with brine (300 mL), and evaporate to a residue. Dissolve in methanol (200 mL), add 7 N ammonia in methanol (100 mL, 700 mmol) and stir at room temperature for 18 hours. Further ammonia can be added if any trifluoracetamide impurity remains. Remove the solvent under reduced pressure and dissolve the residue in aqueous 2 N aqueous hydrochloric acid (1.5 L). Extract with dichloromethane (6×500 mL), combine the organic layers and remove the solvent under reduced pressure to a total volume of about 1 L. Wash with 2 N aqueous hydrochloric acid (300 mL) and combine all aqueous washings. Add 2-methyltetrahydrofuran (1 L) and stir vigorously while adjusting the pH to basic with sodium bicarbonate until no gas evolution is observed. Separate the layers and extract the aqueous with 2-methyltetrahydrofuran (2×500 mL). Dry the combined organic extracts with magnesium sulfate, filter, and evaporate to give a brown solid. Purify the residue by silica gel chromatography eluting with 0-100% dichloromethane in THF. Evaporate the product containing fractions with ethyl acetate/heptane to give the title compound as a fine beige powder (106 g, 70%, 95% purity). ES/MS: m/z 332.0 [M+H], $[\alpha]_D^{20}$=+42.11° (C=0.532, chloroform).

Preparation 29

N-[3-[(4aS,5S,7aS)-2-Benzamido-5-(1,1-difluoroethyl)-4,4a,5,7-tetrahydrofuro[3,4-d][1,3]thiazin-7a-yl]-4-fluoro-phenyl]-5-cyano-pyridine-2-carboxamide

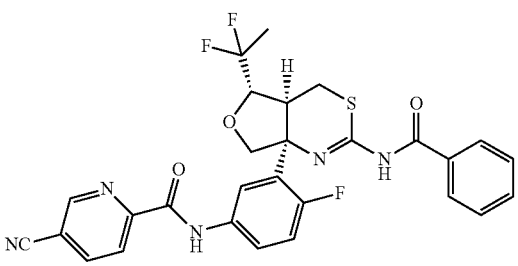 [SMILES: CC(F)(F)[C@H]1OC[C@]2(c3cc(NC(=O)c4ccc(C#N)cn4)ccc3F)N=C(NC(=O)c3ccccc3)SC[C@H]12]

Scheme 3, Step A: Add N,N-diisopropylethylamine (0.032 mL, 0.1837 mmol) to a mixture of N-[(4as,5s,7as)-7a-(5-amino-2-fluoro-phenyl)-5-(1,1-difluoroethyl)-4,4a,5,7-tetrahydrofuro[3,4-d][1,3]thiazin-2-yl]benzamide (0.040 g, 0.09185 mmol), 5-cyanopyridine-2-carboxylic acid (0.0203 g, 0.1378 mmol) and 1-hydroxy-7-azabenzotriazole (0.0191 g, 0.1378 mmol) in dichloromethane (2 ml) and dimethylformamide (0.5 mL). Add 1-(3-dimethylaminopropyl)-3-ethylcarbodiimide hydrochloride (0.026 g, 0.1378 mmol) in one portion. Stir the reaction mixture at ambient temperature for 18 hours. Dilute with ethyl acetate, and wash with water and brine. Extract with ethyl acetate.

Combine the organic extracts and dry over sodium sulfate. Filter and concentrate under reduced pressure to give a residue. Purify the residue by silica gel chromatography, eluting with methyl-tert-butyl ether:dichloromethane (0-10% gradient), to give the title compound (0.0465 g, 90%). ES/MS m/z 566 (M+1).

EXAMPLE 1

N-[3-[(4aS,5S,7aS)-2-Amino-5-(1,1-difluoroethyl)-4,4a,5,7-tetrahydrofuro[3,4-d][1,3]thiazin-7a-yl]-4-fluoro-phenyl]-5-cyano-pyridine-2-carboxamide

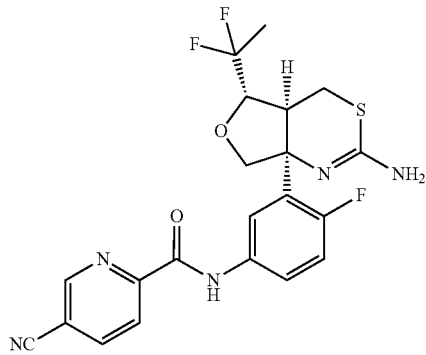 [SMILES: CC(F)(F)[C@H]1OC[C@]2(c3cc(NC(=O)c4ccc(C#N)cn4)ccc3F)N=C(N)SC[C@H]12]

Scheme 3, Step B; Heat at 50° C. for 18 hours a mixture of N-[3-[(4aS,5S,7aS)-2-benzamido-5-(1,1-difluoroethyl)-4,4a,5,7-tetrahydrofuro[3,4-d][1,3]thiazin-7a-yl]-4-fluoro-phenyl]-5-cyano-pyridine-2-carboxamide (0.0465 g, 0.0822 mmol), O-methylhydroxylamine hydrochloride (0.0687 g, 0.8220 mmol) and pyridine (0.066 ml, 0.8220 mmol) in THF (1.5 mL) and ethanol (1.5 mL). Concentrate the mixture under reduced pressure to give a residue. Purify the residue by silica gel chromatography, eluting with 7 N NH₃ in methanol:dichloromethane (0-2% gradient), to give the title compound (0.026 g, 68%). ES/MS m/z 462 (M+1).

EXAMPLE 1A

N-[3-[(4aS,5S,7aS)-2-Amino-5-(1,1-difluoroethyl)-4,4a,5,7-tetrahydrofuro[3,4-d][1,3]thiazin-7a-yl]-4-fluoro-phenyl]-5-cyano-pyridine-2-carboxamide 4-methylbenzenesulfonate hemihydrate (1:1:0.5)

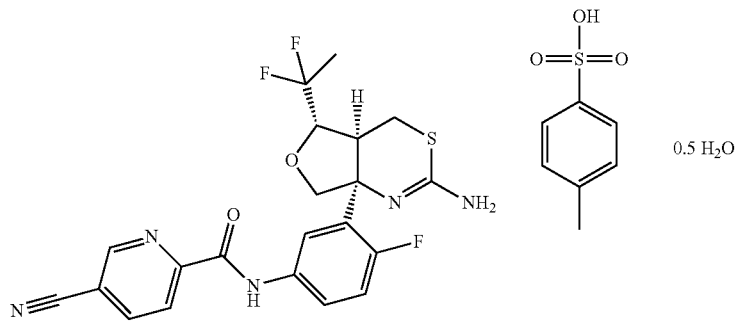 [SMILES: CC(F)(F)[C@H]1OC[C@]2(c3cc(NC(=O)c4ccc(C#N)cn4)ccc3F)N=C(N)SC[C@H]12 ; Cc1ccc(S(=O)(=O)O)cc1]

Add N-[3-[(4aS,5S,7aS)-2-amino-5-(1,1-difluoroethyl)-4,4a,5,7-tetrahydrofuro[3,4-d][1,3]thiazin-7a-yl]-4-fluoro-phenyl]-5-cyano-pyridine-2-carboxamide (150 mg, 0.33 mmol) and THF (2 mL) together and stir at room temperature to dissolve. Add p-toluenesulfonic acid hydrate (0.095 g, 0.5 mmol) and heat the solution to 50° C. Add water in 200 microliter aliquots and observe precipitation after about 2 mL total addition. Stir at 50° C. for several hours to give a thick suspension. Add additional THF (1 mL) to improve mixing. Cool to room temperature over a few hours and filter by vacuum filtration. Wash with minimal THF. Allow to air dry overnight to give the title compound.

Alternate Preparation Example 1a

N-[3-[(4aS,5S,7aS)-2-Amino-5-(1,1-difluoroethyl)-4,4a,5,7-tetrahydrofuro[3,4-d][1,3]thiazin-7a-yl]-4-fluoro-phenyl]-5-cyano-pyridine-2-carboxamide 4-methylbenzenesulfonate hemihydrate (1:1:0.5)

Add N-[3-[(4aS,5S,7aS)-2-amino-5-(1,1-difluoroethyl)-4,4a,5,7-tetrahydrofuro[3,4-d][1,3]thiazin-7a-yl]-4-fluoro-phenyl]-5-cyano-pyridine-2-carboxamide (1.5 g, 3.3 mmol) and THF (12 mL) together and stir at room temperature to dissolve. Heat to 60° C. and add p-toluenesulfonic acid hydrate (0.75 g, 3.96 mmol) and water (5 mL). A white precipitate forms after 5 minutes of stirring. Stir at 60° C. for several hours to give a thick suspension. Cool to room temperature over a few hours and filter by vacuum filtration. Allow to air dry overnight to give the title compound.

X-Ray Powder Diffraction (XRD)

The XRD patterns of crystalline solids are obtained on a Bruker D4 Endeavor X-ray powder diffractometer, equipped with a CuKa source $\lambda=1.54060$ Å) and a Vantec detector, operating at 35 kV and 50 mA. The sample is scanned between 4 and 40° in 2θ, with a step size of 0.009° in 2θ and a scan rate of 0.5 seconds/step, and with 0.6 mm divergence, 5.28 fixed anti-scatter, and 9.5 mm detector slits. The dry powder is packed on a quartz sample holder and a smooth surface is obtained using a glass slide. The crystal form diffraction patterns are collected at ambient temperature and relative humidity. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, are adjusted based on NIST 675 standard peaks at 8.853 and 26.774° 2-theta.

A prepared sample of crystalline N-[3-[(4aS,5S,7aS)-2-amino-5-(1,1-difluoroethyl)-4,4a,5,7-tetrahydrofuro[3,4-d][1,3]thiazin-7a-yl]-4-fluoro-phenyl]-5-cyano-pyridine-2-carboxamide 4-methylbenzenesulfonate hemihydrate (1:1:0.5) is characterized by an XRD pattern using CuKa radiation as having diffraction peaks (2-theta values) as described in Table 1, and in particular having peaks at 6.80 in combination with one or more of the peaks selected from the group consisting of 19.7°, 14.9°, and 10.3°; with a tolerance for the diffraction angles of 0.2 degrees.

TABLE 1

X-ray powder diffraction peaks of the crystalline Example 1a

Example 1a Peak Positions

| Peak | Angle (°2-Theta) +/- 0.2° | Relative Intensity (% of most intense peak) |
|---|---|---|
| 1 | 5.9 | 12.5% |
| 2 | 6.8 | 100.0% |
| 3 | 10.3 | 17.2% |
| 4 | 14.9 | 18.7% |
| 5 | 18.8 | 3.7% |
| 6 | 19.7 | 46.5% |
| 7 | 21.0 | 14.3% |
| 8 | 24.5 | 4.8% |
| 9 | 28.6 | 8.1% |
| 10 | 39.7 | 5.1% |

EXAMPLE 1B

N-[3-[(4aS,5S,7aS)-2-Amino-5-(1,1-difluoroethyl)-4,4a,5,7-tetrahydrofuro[3,4-d][1,3]thiazin-7a-yl]-4-fluoro-phenyl]-5-cyano-pyridine-2-carboxamide methanesulfonate

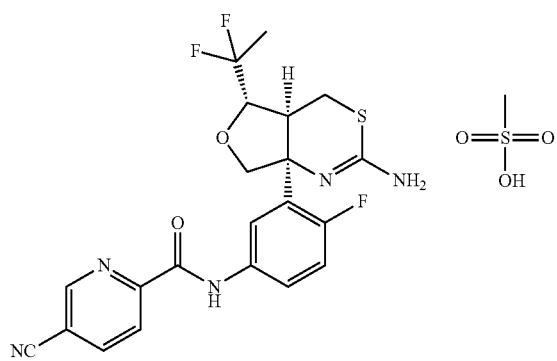

Add N-[3-[(4aS,5S,7aS)-2-amino-5-(1,1-difluoroethyl)-4,4a,5,7-tetrahydrofuro[3,4-d][1,3]thiazin-7a-yl]-4-fluoro-phenyl]-5-cyano-pyridine-2-carboxamide (150 mg, 0.33 mmol) and THF (2 mL) together and stir at room temperature to dissolve. Add methanesulfonic acid (0.095 g, 0.5 mmol) and heat the solution to 50° C. Add water in 200 microliter aliquots up to 2 mL total addition. Stir at 25° C. and precipitation is not observed. Concentrate under nitrogen to volume and a precipitate is observed. Heat the suspension to 60° C. and a clear solution is observed after about 10 minutes. Heat at 60° C. for 1 hour. Cool to room temperature to give a white suspension and stir the mixture for several hours. Isolate the solid by vacuum filtration and wash with a minimal amount of water. Allow to air dry overnight to give the title compound as a crystalline solid.

In Vitro Assay Procedures:

To assess selectivity of BACE1 over BACE2, the test compound is evaluated in FRET and immunoassay detection base enzymatic assays using specific substrates for BACE1 and BACE2 as described below. For in vitro enzymatic and cellular assays, the test compound is prepared in DMSO to make up a 10 mM stock solution. The stock solution is serially diluted in DMSO to obtain a ten-point dilution curve with final compound concentrations ranging from 10 μM to 0.05 nM in a 96-well round-bottom plate before conducting the in vitro enzymatic and whole cell assays.

In Vitro Protease Inhibition Assays:

Expression of huBACE1:Fc and huBACE2:Fc

Human BACE1 (accession number: AF190725) and human BACE2 (accession number: AF 204944) are cloned from total brain cDNA by RT-PCR. The nucleotide sequences corresponding to amino acid sequences #1 to 460 are inserted into the cDNA encoding human IgG$_1$ (Fc) polypeptide (Vassar et al., *Science*, 286, 735-742 (1999)). This fusion protein of BACE1(1-460) or BACE2(1-460) and human Fc, named huBACE1:Fc and huBACE2:Fc respectively, are constructed in the pJB02 vector. Human BACE1 (1-460):Fc (huBACE1:Fc) and human BACE2(1-460):Fc (huBACE2:Fc) are transiently expressed in HEK293 cells. cDNA (250 μg) of each construct are mixed with Fugene 6 and added to 1 liter HEK293 cells. Four days after the transfection, conditioned media are harvested for purification. huBACE1:Fc and huBACE2:Fc are purified by Protein A chromatography as described below. The enzymes are stored at −80° C. in small aliquots. (See Yang, et. al., *J. Neurochemistry*, 91(6) 1249-59 (2004).

Purification of huBACE1:Fc and huBACE2:Fc

Conditioned media of HEK293 cells transiently transfected with huBACE1:Fc or huBACE2:Fc cDNA are collected. Cell debris is removed by filtering the conditioned media through 0.22 μm sterile filter. 5 ml Protein A-agarose (bed volume) is added to 4 liter conditioned media. This mixture is gently stirred overnight at 4° C. The Protein A-agarose resin is collected and packed into a low-pressure chromatography column. The column is washed with 20× bed volumes of PBS at a flow rate 20 ml per hour. Bound huBACE1:Fc or huBACE2:Fc protein is eluted with 50 mM acetic acid, pH 3.6, at flow rate 20 ml per hour. 1 ml fractions of eluent are neutralized immediately with ammonium acetate (0.5 ml 200 mM), pH 6.5. The purity of final product is assessed by electrophoresis in 4-20% Tris-Glycine SDS-PAGE. The enzyme is stored at −80° C. in small aliquots.

BACE1 FRET Assay

Serial dilutions of the test compound are prepared as described above. The compound is further diluted 20× in KH$_2$PO$_4$ buffer. 10 µL of each dilution is added to each well on row A to H of a corresponding low protein binding black plate containing the reaction mixture (25 µL of 50 mM KH$_2$PO$_4$, pH 4.6, 1 mM TRITON® X-100, 1 mg/mL BSA, and 15 M of FRET substrate based upon the sequence of APP) (See Yang, et. al., *J. Neurochemistry*, 91(6) 1249-59 (2004)). The content is mixed well on a plate shaker for 10 minutes. 15 µL of 200 pM human BACE1(1-460):Fc (See Vasser, et al., *Science*, 286, 735-741 (1999)) in the KH$_2$PO$_4$ buffer is added to the plate containing substrate and the test compound to initiate the reaction. The RFU of the mixture at time 0 is recorded at excitation wavelength 355 nm and emission wavelength 460 nm, after brief mixing on a plate shaker. The reaction plate is covered with aluminum foil and kept in a dark humidified oven at room temperature for 16 to 24 hours. The RFU at the end of incubation is recorded with the same excitation and emission settings used at time 0. The difference of the RFU at time 0 and the end of incubation is representative of the activity of BACE1 under the compound treatment. RFU differences are plotted versus inhibitor concentration and a curve is fitted with a four-parameter logistic equation to obtain the IC$_{50}$ value. (May, et al., *Journal of Neuroscience*, 31, 16507-16516 (2011)).

The compound of Example 1 is tested essentially as described above and exhibits an IC$_{50}$ for BACE1 of 0.509 nM±0.104, n=4 (Mean±standard deviation of the mean). This data demonstrates that the compound of Example 1 inhibits purified recombinant BACE1 enzyme activity in vitro.

BACE2 MBP-C125Swe Assay 10 point serial dilutions of test compounds are prepared in the appropriate range. Compounds are further diluted 6× in ammonium acetate assay buffer (50 mmol ammonium acetate, pH 4.6, 1 mM Triton X-100, 1 mg/mL BSA). 10 µL of each dilution is added to each well on row A to H of a corresponding low protein binding plate to which 10 µL of an affinity purified *Escherichia coli* derived substrate (MBPC125swe, 1 µg/mL) for BACE2 activity are pre-added. The content is mixed well on a plate shaker for 10 minutes. 10 µL of 200 picomolar human BACE2 (1-460):Fc in the same reaction buffer described above is added to the plate containing substrate and test compounds to initiate the reaction. After 4 hours, the reaction is stopped by adding stop buffer (40 µL). The amount of product is measured by ELISA using MBP-C26swe standard. Anti-MBP antibody is immobilized on the surface of a high binding polystyrene plate and blocked using a casein/PBS blocking buffer. Sample or standard (40 µL) is added to the ELISA plate and incubated at 4° C. overnight. The plates are then washed and 40 µL of the cleavage specific detection antibody (GN405) is added and allowed to sit for one hour at room temperature. Unbound GN405 is then removed by washing and 40 µL of goat anti-rabbit-HRP conjugate (Southern Biotech, 4010-05) is added to the plate and allowed to sit for 1 hour at room temperature. The plate is again washed and TMB substrate (40 µL) is added. The corresponding amount of product released is a measure of BACE2 activity in the solution at any tested concentration of inhibitor. The 10-point inhibition curve is plotted and fitted with the four-parameter logistic equation to obtain the EC$_{50}$ and IC$_{50}$ values. (See: Sinha, et al., *Nature*, 402, 537-540 (2000)).

The compound of Example 1 is tested essentially as described above and exhibits a BACE2 IC$_{50}$ of 17.6 nM±7.4, n=6 (Mean±standard deviation of the mean). The ratio of BACE1 (FRET IC$_{50}$ enzyme assay) to BACE2 (MBP-C125Swe cell assay) is approximately 35-fold, indicating functional selectivity for inhibiting the BACE1 enzyme. The data set forth above demonstrates that the compound of Example 1 is selective for BACE1 over BACE2.

SH-SY5YAPP695Wt Whole Cell Assay

The routine whole cell assay for the measurement of inhibition of BACE1 activity utilizes the human neuroblastoma cell line SH-SY5Y (ATCC Accession No. CRL2266) stably expressing a human APP695Wt cDNA. Cells are routinely used up to passage number 6 and then discarded.

SH-SY5YAPP695Wt cells are plated in 96 well tissue culture plates at 5.0×10$^4$ cells/well in 200 µL culture media (50% MEM/EBSS and Ham's F12, lx each sodium pyruvate, non-essential amino acids and NaHCO$_3$ containing 10% FBS). The following day, media is removed from the cells, fresh media added then incubated at 37° C. for 24 hours in the presence/absence of test compound at the desired concentration range.

At the end of the incubation, conditioned media are analyzed for evidence of beta-secretase activity by analysis of Abeta peptides 1-40 and 1-42 by specific sandwich ELISAs. To measure these specific isoforms of Abeta, monoclonal 2G3 is used as a capture antibody for Abeta 1-40 and monoclonal 21F12 as a capture antibody for Abeta 1-42. Both Abeta 1-40 and Abeta 1-42 ELISAs use biotinylated 3D6 as the reporting antibody (for description of antibodies, see Johnson-Wood, et al., *Proc. Natl. Acad. Sci. USA* 94, 1550-1555 (1997)). The concentration of Abeta released in the conditioned media following the compound treatment corresponds to the activity of BACE1 under such conditions. The 10-point inhibition curve is plotted and fitted with the four-parameter logistic equation to obtain the IC$_{50}$ values for the Abeta-lowering effect.

The compound of Example 1 is tested essentially as described above and exhibits an IC$_{50}$ of 0.157 nM±0.048, n=4 for SH-SYSYAPP695Wt A-beta (1-40) ELISA and an IC$_{50}$ of 0.177 nM±0.050, n=4 for SH-SY5YAPP695Wt A-beta (1-42) ELISA (Mean±standard deviation of the mean). The data set forth above demonstrates that the compound of Example 1 inhibits BACE1 in the whole cell assay.

In Vivo Inhibition of Beta-Secretase

Several animal models, including mouse, guinea pig, dog, and monkey, may be used to screen for inhibition of beta-secretase activity in vivo following compound treatment. Animals used in this invention can be wild type, transgenic, or gene knockout animals. For example, the PDAPP mouse model, prepared as described in Games et al., *Nature* 373, 523-527 (1995), and other non-transgenic or gene knockout animals are useful to analyze in vivo inhibition of Abeta and sAPPbeta production in the presence of inhibitory compounds. Generally, 2 month old PDAPP mice, gene knock-out mice or non-transgenic animals are administered compound formulated in vehicles, such as corn oil, beta-cyclodextran, phosphate buffers, PHARMASOLVE®, or other suitable vehicles via oral, subcutaneous, intra-venous, feeding, or other route of administration. 1 to 24 hours following the administration of compound, animals are sacrificed, and brains are removed for analysis of Abeta 1-x. "Abeta 1-x" as used herein refers to the sum of Abeta species that begin with residue 1 and end with a C-terminus greater than residue 28. This detects the majority of Abeta species and is often called "total Abeta". Total Abeta peptides (Abeta 1-x) levels are measured by a sandwich ELISA, using monoclonal 266 as a capture antibody and biotinylated 3D6 as reporting antibody. (See May, et al., *Journal of Neuroscience,* 31, 16507-16516 (2011)).

For acute studies, compound or appropriate vehicle is administered and animals are sacrificed at about 3 hours after dosing. Brain tissue, is obtained from selected animals and analyzed for the presence of Abeta 1-x. After chronic dosing brain tissues of older APP transgenic animals may also be analyzed for the amount of beta-amyloid plaques following compound treatment.

Animals (PDAPP or other APP transgenic or non-transgenic mice) administered an inhibitory compound may demonstrate the reduction of Abeta in brain tissues, as compared with vehicle-treated controls or time zero controls. For example, a 0.1, 0.3, and 1 mg/kg oral dose of Example 1, to young female PDAPP mice reduced Abeta 1-x peptide levels in brain hippocampus by 32%, 40%, and 55% (all values p<0.01), respectively. In brain cortical tissue, doses of 0.1, 0.3, and 1 mg/kg of Example 1 reduced Abeta 1-x levels by 38%, 50%, and 67% (all values p<0.01) compared to vehicle-treated mice three hours after dosing.

Given the activity of the compound of Example 1 against the BACE1 enzyme in vitro, these Abeta-lowering effects are consistent with BACE1 inhibition in vivo, and further demonstrate CNS penetration of the compound of Example 1.

These studies show that compounds of the present invention inhibit BACE1 and are, therefore, useful in reducing Abeta levels.

We claim:

1. A compound of the formula:

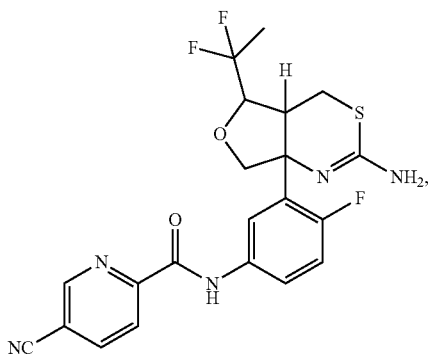 [SMILES: CC(F)(F)C1OCC2(c3cc(NC(=O)c4ccc(C#N)cn4)ccc3F)N=C(N)SCC12]

or a pharmaceutically acceptable salt thereof.

2. The compound or salt thereof according to claim 1 wherein the compound is:

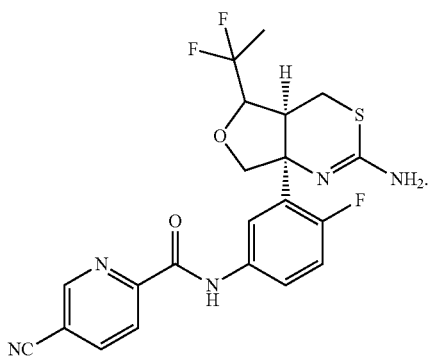 [SMILES: CC(F)(F)[C@H]1OC[C@]2(c3cc(NC(=O)c4ccc(C#N)cn4)ccc3F)N=C(N)SC[C@H]12]

3. The compound or salt thereof according to claim 2 wherein the compound is:

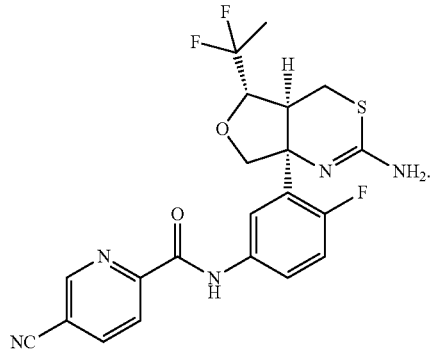

4. The salt according to claim 3 which is:

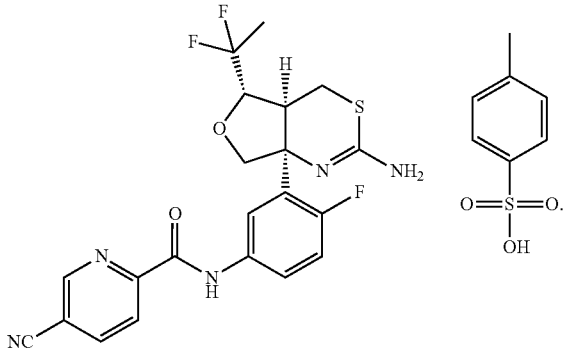 [SMILES: CC(F)(F)[C@H]1OC[C@]2(c3cc(NC(=O)c4ccc(C#N)cn4)ccc3F)N=C(N)SC[C@H]12 ; Cc1ccc(S(=O)(=O)O)cc1]

5. The salt according to claim 3 which is:

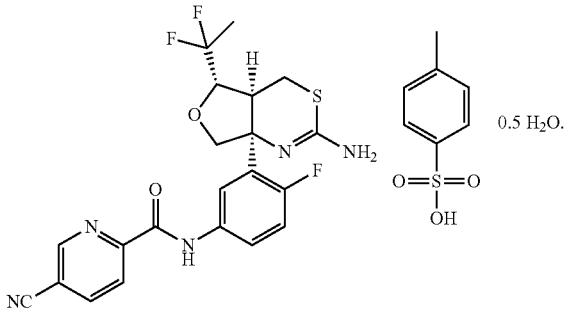 [SMILES: CC(F)(F)[C@H]1OC[C@]2(c3cc(NC(=O)c4ccc(C#N)cn4)ccc3F)N=C(N)SC[C@H]12 ; Cc1ccc(S(=O)(=O)O)cc1]

6. The salt according to claim 3 which is:

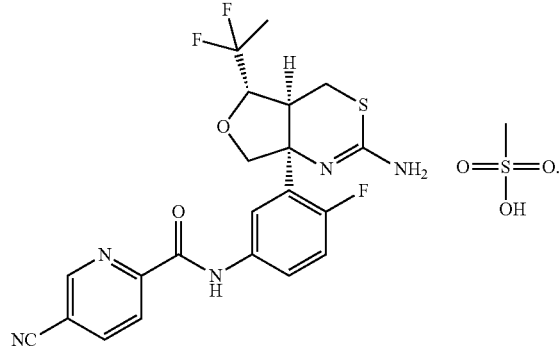

7. The compound or salt thereof according to claim 3 wherein the compound is N-[3-[(4aS,5S,7aS)-2-amino-5-(1, 1-difluoroethyl)-4,4a,5,7-tetrahydrofuro[3,4-d][1,3]thiazin-7a-yl]-4-fluoro-phenyl]-5-cyano-pyridine-2-carboxamide.

8. The compound according to claim 3 which is N-[3-[(4aS,5S,7aS)-2-amino-5-(1,1-difluoroethyl)-4,4a,5,7-tetrahydrofuro[3,4-d][1,3]thiazin-7a-yl]-4-fluoro-phenyl]-5-cyano-pyridine-2-carboxamide.

9. The salt according to claim 4 which is N-[3-[(4aS,5S,7aS)-2-amino-5-(1,1-difluoroethyl)-4,4a,5,7-tetrahydrofuro[3,4-d][1,3]thiazin-7a-yl]-4-fluoro-phenyl]-5-cyano-pyridine-2-carboxamide 4-methylbenzenesulfonate.

10. The salt according to claim 4 which is N-[3-[(4aS,5S,7aS)-2-Amino-5-(1,1-difluoroethyl)-4,4a,5,7-tetrahydrofuro[3,4-d][1,3]thiazin-7a-yl]-4-fluoro-phenyl]-5-cyano-pyridine-2-carboxamide 4-methylbenzenesulfonate hemihydrate.

11. The salt according to claim 10 which is characterized by a substantial peak in the X-ray diffraction spectrum, at diffraction angle 2-theta of 6.8° in combination with one or more of the peaks selected from the group consisting of 19.7°, 14.9°, and 10.3°; with a tolerance for the diffraction angles of 0.2 degrees.

12. The salt according to claim 6 which is N-[3-[(4aS,5S,7aS)-2-amino-5-(1,1-difluoroethyl)-4,4a,5,7-tetrahydrofuro[3,4-d][1,3]thiazin-7a-yl]-4-fluoro-phenyl]-5-cyano-pyridine-2-carboxamide methanesulfonate.

13. A method of treating Alzheimer's disease in a patient, comprising administering to a patient in need of such treatment an effective amount of a compound of claim 1, or a pharmaceutically acceptable salt thereof.

14. A method of treating the progression of mild cognitive impairment to Alzheimer's disease in a patient, comprising administering to a patient in need of such treatment an effective amount of a compound of claim 1, or a pharmaceutically acceptable salt thereof.

15. A pharmaceutical composition, comprising a compound or a pharmaceutically acceptable salt thereof according to claim 1 with one or more pharmaceutically acceptable carriers, diluents, or excipients.

16. A process for preparing a pharmaceutical composition, comprising admixing a compound or a pharmaceutically acceptable salt thereof according to claim 1 with one or more pharmaceutically acceptable carriers, diluents, or excipients.

17. A method of treating Alzheimer's disease in a patient, comprising administering to a patient in need of such treatment an effective amount of a compound of claim 3, or a pharmaceutically acceptable salt thereof.

18. A method of treating the progression of mild cognitive impairment to Alzheimer's disease in a patient, comprising administering to a patient in need of such treatment an effective amount of a compound of claim 3, or a pharmaceutically acceptable salt thereof.

19. A pharmaceutical composition, comprising a compound or a pharmaceutically acceptable salt thereof according to claim 3 with one or more pharmaceutically acceptable carriers, diluents, or excipients.

20. A process for preparing a pharmaceutical composition, comprising admixing a compound or a pharmaceutically acceptable salt thereof according to claim 3 with one or more pharmaceutically acceptable carriers, diluents, or excipients.

* * * * *